(12) United States Patent
Tsumuki et al.

(10) Patent No.: US 6,306,847 B1
(45) Date of Patent: *Oct. 23, 2001

(54) CONDENSED PURINE DERIVATIVES

(75) Inventors: Hiroshi Tsumuki, Sakai; Mayumi Saki, Numazu; Hiromi Nonaka, Shizuoka; Michio Ichimura, Mishima; Junichi Shimada, Shizuoka; Fumio Suzuki, Mishima; Shunji Ichikawa; Nobuo Kosaka, both of Shizuoka, all of (JP)

(73) Assignee: Kyowa Hakko Kogyo Co., Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/090,936

(22) Filed: Jun. 5, 1998

Related U.S. Application Data

(63) Continuation-in-part of application No. PCT/JP97/03586, filed on Oct. 7, 1997.

(30) Foreign Application Priority Data

Oct. 7, 1996 (JP) .................................................. 26-581896

(51) Int. Cl.[7] ...................... C07D 487/14; A61K 31/519; A61K 31/551; A61P 11/06; A61P 11/08

(52) U.S. Cl. .......................... 514/183; 514/220; 514/267; 540/471; 540/559; 544/251; 544/276

(58) Field of Search ................................... 540/471, 559; 544/251; 514/220, 183, 267

(56) References Cited

U.S. PATENT DOCUMENTS

| | | | |
|---|---|---|---|
| 5,270,316 | 12/1993 | Suzuki et al. | 514/267 |
| 5,646,156 | 7/1997 | Jacobson et al. | 514/263 |

FOREIGN PATENT DOCUMENTS

WO 95/11681   5/1998  (WO).

OTHER PUBLICATIONS

Grant & Hackh's Chemical Dictionary 5th Edition, p. 444, 1991.*

B. Fredholm, et al, VI. Nomenclature and Classification of Purinoceptors, *Pharmacological Reviews*, vol. 46, No. 2, pp. 143–156. (1994).

C.A. Salvatore, et al, Molecular Cloning and Characterization of the Human $A_3$ Adenosine Receptor, *Proc. Natl. Acad, Sci. USA*, vol. 90, pp. 10365–10369 Nov. 1993.

V. Ramkumar, et al, The $A_3$ Adenosine Receptor is the Unique Adenosine Receptor which Facilitates Release of Allergic Mediators in Mast Cell, *The Journal of Biological Chemistry*, vol. 268, No. 23, 8/93, pp 16887–16890.

D.L. Temple, Jr., et al, Substituted 6,7–Dihydroimidazo[1,2–a]purin–9(4H)–ones *J. Med. Chem.,American Chemical Society*, vol. 23, 1980, pp. 1188–1198.

Chem Abstracts File Registry Printout for glycerophosphocholine.*

Chem Abstracts File Registry Printout for methylphosphoethanolamine.*

Chem Abstracts File Registry Printout for phosphocholine.*

Chem Abstracts File Registry Printout for phosphoethanolamine.*

Chem Abstracts File Registry Printout for phosphoarginine A.*

Chem Abstracts File Registry Printout for phosphoamidofluoridothioic acid.*

Chem Abstracts File Registry Printout for phosphothiamine.*

Chem Abstracts File Registry Printout for phosphohydroxypyruvic acid.*

* cited by examiner

*Primary Examiner*—Mark L. Berch
(74) *Attorney, Agent, or Firm*—Antonelli, Terry, Stout & Kraus, LLP

(57) ABSTRACT

The present invention provides condensed purine derivatives or pharmacologically acceptable salts thereof exhibiting adenosine $A_3$ acceptor antagonising activity, and having an antiasthmatic action, a bronchodilator action, an antiantiitching action, etc., and represented by the following formula (I):

(wherein $R^1$ represents substituted or unsubstituted aryl or a substituted or unsubstituted aromatic heterocyclic group; $R^2$ represents hydrogen, lower alkyl, alicyclic alkyl, substituted or unsubstituted aralkyl, substituted or unsubstituted aryl, or a substituted or unsubstituted aromatic heterocyclic group; $R^3$ represents hydrogen, lower alkyl, or substituted or unsubstituted aralkyl; $X^1$ and $X^2$ are the same or different and each represents hydrogen, lower alkyl, substituted or unsubstituted aralkyl, or substituted or unsubstituted aryl; and n represents an integer of 0 to 3).

7 Claims, No Drawings

CONDENSED PURINE DERIVATIVES

CROSS REFERENCE TO RELATED APPLICATION

This application is a continuation-in-part of PCT Patent Application No. PCT/JP97/03586, filed Oct. 7, 1997.

TECHNICAL FIELD

The present invention relates to condensed purine derivatives exhibiting adenosine $A_3$ receptor antagonising activity, and having an antiasthmatic action, a bronchodilator action, an antiallergic action, an anti-itching action, etc.

BACKGROUND ART

Adenosine binds to adenosine receptors at the cell surfaces to cause various biological response.

The four subtypes of adenosine receptors, including $A_1$, $A_{2a}$, $A_{2b}$ and $A_3$ are known to be present (Pharmacological Reviews, Vol. 46, No. 2, p143, 1994). It is indicated that adenosine $A_3$ receptors are highly represented in the human pulmonary tissue (Proc. Natl. Acad. Sci. USA, Vol. 90, p10365, 1993), and are related to acceleration of the release of various mediators from mast cells (J. Biol. Chem., Vol. 268, No. 23, p16887, 1993). It is also disclosed in WO 95/11681 that compounds antagonistic to $A_3$ receptors inhibit mast cell degranulation by adenosine and are 2288733A that compounds antagonistic to $A_3$ receptors inhibit the activation of eosinophil by adenosine and are expected as antiasthmatics. Namely, compounds antagonistic to adenosine $A_3$ receptors are expected as antiasthmatics. Allergic diseases such as pruritus are known to be caused by the release of mediators from mast cells due to various types of stimulation [Standard Dermatology, Vol. 4. p160 (Igakushoin), 1994]. Therefore, compounds antagonistic to $A_3$ receptors are also expected to inhibit the release of mediators from mast cells and exhibit an antiallergic action such as an antipruritic action or the like.

A paper ( J. Med. Chem., Vol. 23, p1188, 1980) discloses that as condensed purine compounds, compounds represented by formula (A) have a weak bronchodilator action. Also Japanese Unexamined Patent Publication No. 91-204880 discloses that compounds represented by formula (B) exhibit a diuretic action and a weak antiasthmatic action.

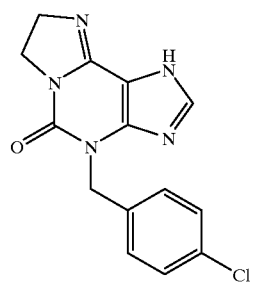

(A)

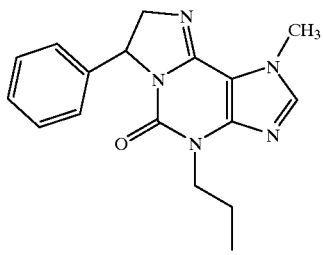

(B)

DISCLOSURE OF INVENTION

An object of the present invention is to provide novel condensed purine derivatives exhibiting adenosine $A_3$ receptor antagonising activity, and having an antiasthmatic action, a bronchodilator action, an antiallergic action, an antiitching action, etc.

The present invention relates to condensed purine compounds and pharmacologically acceptable salts thereof represented by the following formula (I):

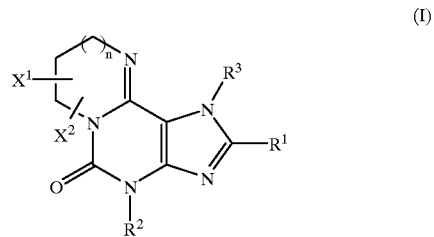

(I)

(wherein $R^1$ represents substituted or unsubstituted aryl or a substituted or unsubstituted aromatic heterocyclic group; $R^2$ represents hydrogen, lower alkyl, alicyclic alkyl, substituted or unsubstituted aralkyl, substituted or unsubstituted aryl, or a substituted or unsubstituted aromatic heterocyclic group; $R^3$ represents hydrogen, lower alkyl, or substituted or unsubstituted aralkyl; $X^1$ and $X^2$ are the same or different and each represents hydrogen, lower alkyl, substituted or unsubstituted aralkyl, or substituted or unsubstituted aryl; and n represents an integer of 0 to 3).

Hereinafter, compounds represented by formula (I) are referred to as "compounds (I)". This applies to compounds represented by other formulas.

In the definition of each of the groups in formula (I), lower alkyl includes straight or branched groups having 1 to 9 carbon atoms, such as methyl, ethyl, propyl, isopropyl, butyl, isobutyl, sec-butyl, tert-butyl, pentyl, neopentyl, hexyl, heptyl, octyl, nonyl, and the like. Alicyclic alkyl includes groups having 3 to 8 carbon atoms, such as cyclopropyl, cyclobutyl, cyclopentyl, cyclohexyl, cycloheptyl, cyclooctyl, and the like. Aralkyl includes groups having 7 to 15 carbon atoms, such as benzyl, phenethyl, benzhydryl, naphthylmethyl, and the like. Aryl includes phenyl, naphthyl, indenyl, anthranyl, and the like. Aromatic heterocyclic groups include furyl, thienyl, pyrrolyl, imidazolyl, pyrazolyl, triazolyl, tetrazolyl, oxazolyl, thiazolyl, pyridyl, pyrazinyl, pyrimidinyl, pyridazinyl, triazinyl, indolyl, indazolyl, benzoimidazolyl, benzoxazolyl, benzothiazolyl, quinolyl, isoquinolyl, phthalazinyl, naphthyridinyl, quinoxalinyl, quinazolinyl, cinnolinyl, purinyl, and the like.

Each of substituted aryl, aralkyl, and aromatic heterocyclic groups has 1 to 3 substituents which are the same or different, and which are selected from, substituted or unsubstituted lower alkyl, substituted or unsubstituted lower alkenyl, substituted or unsubstituted lower alkinyl, substituted or unsubstituted aralkyl, substituted or unsubstituted aryl, hydroxy, substituted or unsubstituted lower alkoxy, substituted or unsubstituted aralkyloxy, substituted or unsubstituted aryloxy, lower alkxoylcarbonyl, lower alkylthio, lower alkylsulfonyl, carboxy, carbamoyl, lower alkanoyl, aroyl, halogen, nitro, amino, mono- or di-lower alkylamine, cyano, trifluoromethyl, and the like. Of these substituents, lower alkyl and the lower alkyl moiety of each of lower alkoxy, lower alkoxycarbonyl, lower alkylthio, lower alkylsulfonyl, lower alkanoyl, and mono- or di-alkylamino are defined in the same way as defined above for lower alkyl. Aralkyl and the aralkyl moiety in the of aralkyloxy are defined in the same as defined above for aralkyl. Aryl and the aryl moiety in each of aryloxy and aroyl are defined in the same way as defined above for aryl.

Lower alkenyl includes straight or branched groups having 2 to 6 carbon atoms, such as vinyl, ally, 1-propenyl, methacryl, butenyl, crotyl, pentenyl, hexenyl, and the like.

Lower alkynyl includes straight or branched groups having 2 to 6 carbon atoms, such as ethynyl, propynyl, butynyl, pentynyl, hexynyl, and the like.

Halogen includes fluorine, chlorine, bromine and iodine atoms. Each of substituted lower alkyl, substituted lower alkenyl, substituted lower alkynyl and substituted lower alkoxy has 1 to 3 are selected from which are the same or different and which are, for example, carboxy, sulfo, phospho, lower alkyl esters, aralkyl eaters or aryl esters thereof, hydroxy, halogen and the like. Each of the lower alkyl moiety of lower alkyl esters, the aralkyl moiety of aralkyl esters and the aryl moiety in aryl esters is defined in the same way as defined above. Halogen is defined as the same as the above. Each of substituted aralkyl, substituted aryl, substituted aralkyloxy and substituted aryloxy has 1 to 3 substituents which are the same or different, and are selected from lower alkyl, hydroxy, halogen and the like. Lower alkyl and halogen are defined as the same as the above.

As compounds (I), compounds having hydrogen as $R^3$ are preferable, and compounds having substituted or unsubstituted phenyl as $R^1$ are preferable. Where $R^1$ is substituted phenyl, compounds having 1 to 3 substituents in substituted phenyl as $R^1$, which are the same or different and are selected from halogen, lower alkyl, lower alkoxy and substituted lower alkenyl, are preferred, and halogen is particularly prefered. As the substituent of substituted lower alkenyl, lower alkoxycarbonyl is prefered.

Pharmacologically acceptable salts of compounds (I) include pharmacologically acceptable metal salts, ammonium salts, organic amine addition salts, amino acid addition salts, acid addition salts, and the like.

Pharmacologically acceptable metal salts of compounds (I) include alkali metal salts such as sodium salts, potassium salts, and the like; alkaline earth metal salts such as magnesium salts, calcium salts, and the like; aluminum salts; zinc salts; and the like. Pharmacologically acceptable ammonium salts include ammonium, tetramethylammonium, and the like. Pharmacologically acceptable organic amine addition salts include addition salts of morpholine, piperidine, and the like. Pharmacologically acceptable amino acid addition salts include addition salts of lysine, glycine, phenylalanine, and the like. Pharmacologically acceptable acid addition salts include inorganic acid salts such as hydrochlorides, sulfates, phosphates, and the like; organic acid salts such as acetates, maleates, fumarates, tartrates, citrates, and the like.

The process for producing compounds (I) will be described below.

Process 1

Compounds (I) can be produced according to the following reaction steps:

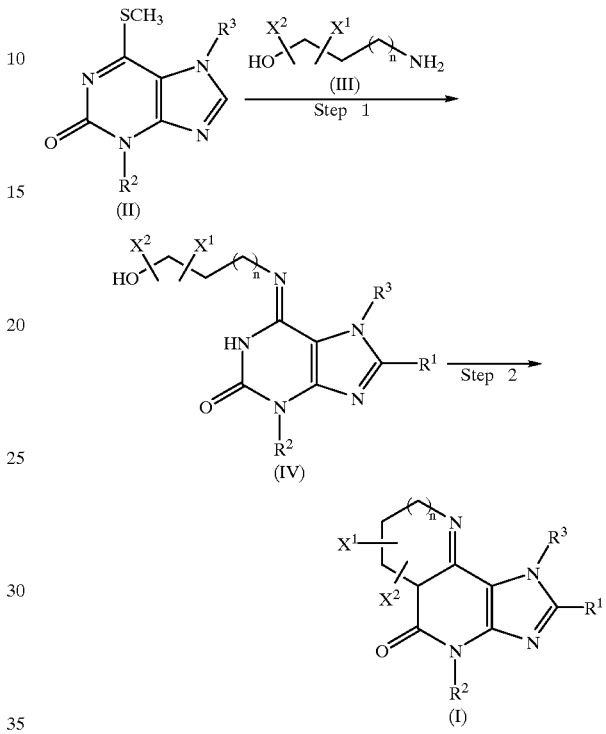

(wherein $R^1$, $R^2$, $R^3$, $X^1$, $X^2$ and n are defined in the same way as defined above).

Step 1

Compound (IV) can be obtained by reacting compound (II) with 1 to 10 equivalents, preferably 4 to 6 equivalents, of compound (III) without a solvent or in an appropriate solvent. Examples of the solvent include dimethylamides such as dimethylformamide, dimethylacetamide, and the like; ketones such as acetone, methyl ethyl ketone, and the like; aromatic hydrocarbons such as toluene, xylene, and the like; halogenated hydrocarbons such as dichloromethane, 1,1,2,2-tetrachloroethane, and the like; dimethyl sulfoxide; and the like. Dimethyl sulfoxide is prefered. These solvents are used singly or in mixture. The reaction is carried out at 50 to 180° C. for 5 minutes to 24 hours.

Compound (II) as a starting material can be obtained by a known method (J. Chem. Soc. Perkin I, p739, 1973), or in accordance with this method.

Step 2

Compound (I) can be obtained by treating compound (IV) with 1 equivalent to an excessive amount, preferably excessive amount, of halogenating agent such as thionyl chloride, phosphorus oxychloride, or the like, or an inorganic salt such as hydrochloric acid, hydrobromic acid, hydroiodic acid, phosphoric acid, or the like without a solvent or in an appropriate solvent. The Examples of solvents includes, for example, halogenated hydrocarbons such as methylene chloride, chloroform, dichloroethane, and the like; dimethylformamide; dimethyl sulfoxide; and the like. Chloroform is prefered. These solvents are used singly or in mixture. The reaction is carried out at −10 to 150° C., preferably 50 to 70° C., for 5 minutes to 24 hours.

Process 2

Of compounds (I), compound (Ia) in which $R^1$ is β-lower alkoxycarbonylstyryl, β-aralkyloxycarbonylstyryl or β-aryloxycarbonylstyryl, and $R^3$ is hydrogen, or compound (Ib) in which $R^1$ is β-carboxystyryl and $R^3$ is hydrogen can also be produced in accordance with the following reaction steps:

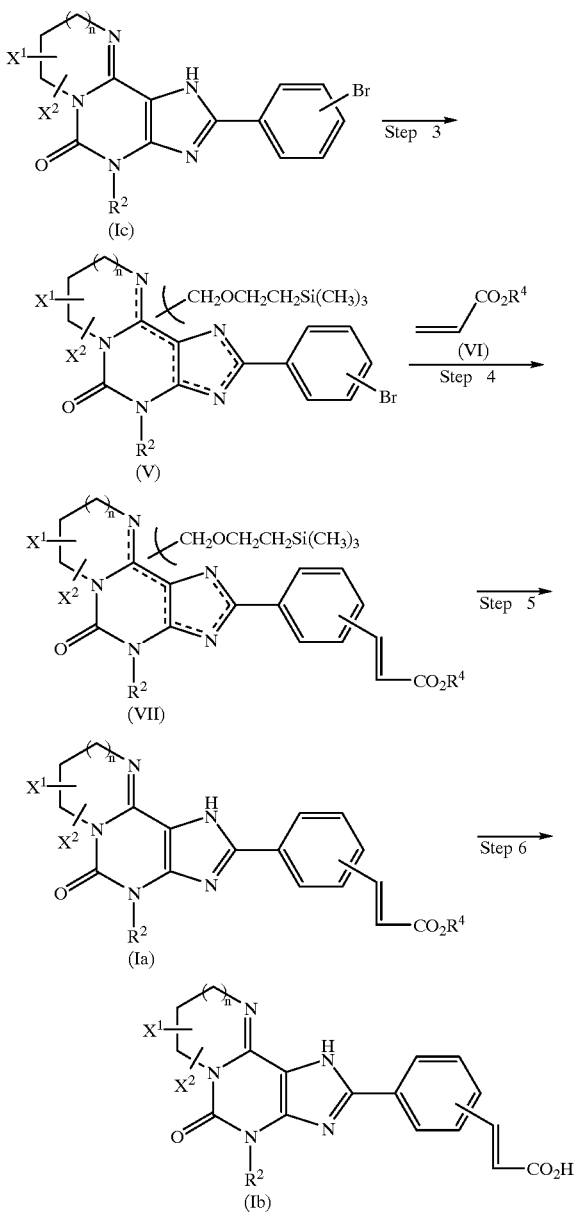

(wherein $R^4$ represents alkyl, aralkyl or aryl, and $R^2$, $X^1$, $X^2$ and n are defined in the same way as defined above).

In the definition of $R^4$, each of lower alkyl, aralkyl and aryl is defined in the same way as defined above.

Step 3

Compound (V) can be obtained by reacting compound (Ic) which is compound (I) in which $R^1$ is bromophenyl, and $R^3$ is hydrogen, with 1 to 3 equivalents of 2-(chloromethoxy) ethyltrimethylsilane in the presence of 3 to 10 equivalents of an appropriate base without a solvent or in an appropriate solvent. Examples of the base include triethylamine, diisopropylethylamine, or the like. Triethylamine is prefered. Examples of the solvent include dimethylammides such as dimethylformamide, dimethylacetamide, and the like; ketones such as acetone, methyl ethyl ketone, and the like; aromatic hydrocarbons such as toluene, xylene, and the like; ethers such as tetrahydrofuran, dioxane, ether, and the like; pyridine; acetonitrile; dimethyl sulfoxide; and the like. Tetrahydrofuran or dimethyl sulfoxide is preferably used. The reaction is generally carried out at 0 to 50° C., preferably at room temperature, for 30 minutes to 24 hours.

Step 4

Compound (VII) can be obtained by reacting compound (V) with one equivalent to an excessive amount of compound (VI) in the presence of 1 to 5 equivalents of an appropriate base and a catalytic amount of palladium catalyst without a solvent or in an appropriate solvent. Examples of the base include triethylamine, diisopropylamine, pyridine, potassium carbonate, sodium carbonate, sodium hydrogen carbonate, and the like. Triethylamine is prefered. Examples of the palladium catalyst include tetrakistriphenylphosphine palladium, dichloropalladium, palladium acetate, and the like. Dichlorobistriphenylphosphine palladium is preferably used. Examples of the solvent include dimethyamides such as dimethylformamide, dimethylacetamide, and the like; ketones such as acetone, methyl ethyl ketone, and the like; aromatic hydrocarbons such as toluene, xylene, and the like; ethers such as tetrahydrofuran, dioxane, ether, and the like; acetonitrile; dimethyl sulfoxide; and the like. Dimethylformamide is preferably used. The reaction is generally carried out at 0 to 150° C., preferably 90 to 110° C., for 10 minutes to 24 hours.

Step 5

Compound (Ia) can be obtained by treating compound (VII) with an inorganic acid such as hydrochloric acid or the like without a solvent or in an appropriate solvent. Examples of the solvent include alcohols such as ethanol, methanol, propanol, and the like; dimethylamides such as dimethylformamide, dimethylacetamide, and the like; ketones such as acetone, methyl ethyl ketone, and the like; ethers such as tetrahydrofuran, dioxane, ether, and the like; halogenated hydrocarbons such as methylene chloride, chloroform, dichloroethane, and the like; acetonitrile; dimethyl sulfoxide; water; and the like. Ethanol or dioxane is preferably used. The reaction is generally carried out at 0 to 100° C., preferably room temperature, for 5 minutes to 24 hours.

Compound (Ia) can also be obtained by the following method:

Compound (Ia) can be obtained by treating compound (VII) with tetrabutylammonium fluoride or the like in an appropriate solvent. Examples of the solvent include alcohols such as ethanol, methanol, propanol, and the like; dimethylamides such as dimethylformamide, dimethylacetamide, and the like; ketones such as acetone, methyl ethyl ketone, and the like; ethers such as tetrahydrofuran, dioxane, ether, and the like; acetonitrile; dimethyl sulfoxide; water; and the like. Tetrahydrofuran is preferably used. The reaction is generally performed at 0 to 80° C., preferably room temperature, for 5 minutes to 24 hours.

Step 6

Compound (Ib) can be obtained by treating compound (Ia) with a 1 to 10N sodium hydroxide aqueous solution without a solvent or in an appropriate solvent. Examples of the solvent include alcohols such as ethanol, methanol, propanol, and the like; dimethylamides such as dimethylformamide, dimethylacetamide, and the like; ketones such as acetone, methyl kethyl ketone, and the like; ethers such as tetrahydrofuran, dioxane, ether, and the like; acetonitrile; dimethyl sulfoxide; water; and the like. Ethanol or dioxane is preferably used. The treatment is generally effected at 0 to 100° C., preferably at room temperature, for 5 minutes to 24 hours.

Of compounds (I), compound (Id) in which $R^1$ is β-lower alkoxycarbonylstyryl, β-aralkyloxycarbonylstyryl or β-aryloxycarbonylstyryl, and $R^3$ is lower alkyl or substituted or unsubstituted aralkyl can also be produced from a compound as compound (I) in which $R^1$ is bromophenyl and $R^3$ is lower alkyl or substituted or unsubstituted aralkyl in accordance with the process of Step 4. Of compounds (I), compound (Ie) in which $R^1$ is β-carbonylstyryl and $R^3$ is lower alkyl or substituted or unsubstituted aralkyl can also be produced from compound (Id) in accordance with the process of Step 6.

The intermediate and target compound in each of the above processes can be isolated and purified by a purification method generally used in synthetic organic chemistry, for example, neutralization, filtration, extraction, washing, drying, concentration, recrystallization, various chromatographic methods. The intermediates can be supplied to the subsequent reaction without particular purification.

In order to obtain salts of compounds (I), a general method of synthetic organic chemistry may be used. For example, when compounds (I) are obtained as salts, the salts may be purified, and when compounds (I) are obtained in a free form, compounds (I) may be dissolved or suspended in an appropriate solvent, and then an acid or base may be added to form salts.

Some compounds (I) have geometric isomers or optical isomers. The present invention include all possible stereoisomers including geometric isomers and optical isomers, and mixtures thereof.

Some compounds (I) or pharmacologically acceptable salts thereof are present in the form of an adduct with water or one of various solvents. The present invention include these adducts.

Table 1 shows examples of compounds (I). In this table, compounds of Compound No. 1 to 38 correspond to compounds obtained in Examples 1 to 38, respectively, which will be described below.

TABLE 1-1

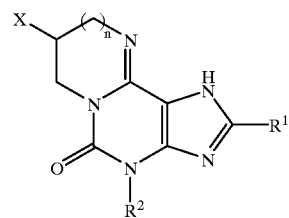

| Compound No. | $R^1$ | $R^2$ | n | X |
|---|---|---|---|---|
| 1 | 4-Br-phenyl | $CH_2CH_3$ | 0 | H |
| 2 | 4-Br-phenyl | $CH_2CH_3$ | 1 | H |
| 3 | 4-Br-phenyl | $CH_2CH_3$ | 0 | $CH_3$ |
| 4 | 4-Br-phenyl | $CH_2CH_3$ | 0 | $CH_2CH_3$ |
| 5 | 4-Br-phenyl | $(CH_2)_2CH_3$ | 0 | H |
| 6 | 4-Br-phenyl | $(CH_2)_2CH_3$ | 1 | H |
| 7 | 4-Br-phenyl | $(CH_2)_2CH_3$ | 0 | $CH_3$ |
| 8 | 4-Br-phenyl | $(CH_2)_2CH_3$ | 0 | $CH_2CH_3$ |
| 9 | 2-Br-phenyl | $(CH_2)_2CH_3$ | 0 | H |
| 10 | 4-$CH_3$-phenyl | $(CH_2)_2CH_3$ | 0 | H |
| 11 | 2-Br-phenyl | $(CH_2)_2CH_3$ | 0 | $CH_2CH_3$ |

TABLE 1-1-continued
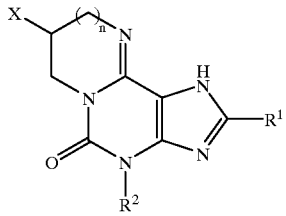
| Compound No. | R¹ | R² | n | X |
|---|---|---|---|---|
| 12 | 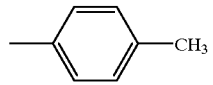 | (CH$_2$)$_2$CH$_3$ | 0 | CH$_2$CH$_3$ |
TABLE 1-2
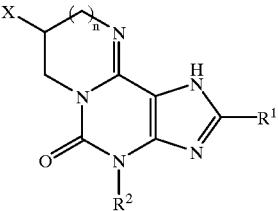
| Compound No. | R¹ | R² | n | X |
|---|---|---|---|---|
| 13 | 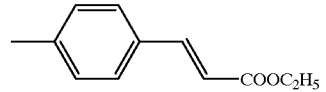 | CH$_2$CH$_3$ | 0 | H |
| 14 | 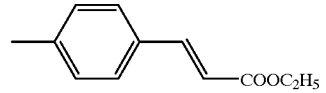 | CH$_2$CH$_3$ | 1 | H |
| 15 | 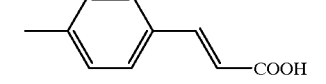 | CH$_2$CH$_3$ | 1 | H |
| 16 | 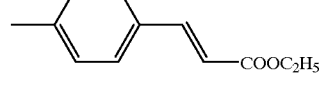 | CH$_2$CH$_3$ | 0 | CH$_2$CH$_3$ |
| 17 | 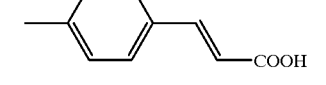 | CH$_2$CH$_3$ | 0 | CH$_2$CH$_3$ |
| 18 | 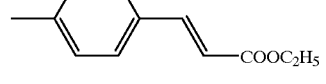 | (CH$_2$)$_2$CH$_3$ | 0 | H |
| 19 | 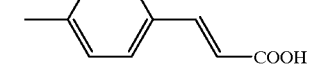 | (CH$_2$)$_2$CH$_3$ | 0 | H |

TABLE 1-2-continued

| Compound No. | R¹ | R² | n | X |
|---|---|---|---|---|
| 20 | 4-(CH=CH-COOC₂H₅)-phenyl | (CH₂)₂CH₃ | 0 | CH₂CH₃ |
| 21 | 4-(CH=CH-COOH)-phenyl | (CH₂)₂CH₃ | 0 | CH₂CH₃ |

TABLE 1-3

| Compound No. | R¹ | R² | n | X |
|---|---|---|---|---|
| 22 | 3-Br-phenyl | (CH₂)₂CH₃ | 0 | H |
| 23 | 3-Br-phenyl | (CH₂)₂CH₃ | 0 | CH₂CH₃ |
| 24 | phenyl | (CH₂)₂CH₃ | 0 | CH₂CH₃ |
| 25 | 4-Br-phenyl | CH₃ | 0 | CH₂CH₃ |
| 26 | 4-Br-phenyl | (CH₂)₃CH₃ | 0 | H |
| 27 | 4-Br-phenyl | (CH₂)₃CH₃ | 0 | CH₂CH₃ |
| 28 | 4-Br-phenyl | phenyl | 0 | CH₂CH₃ |
| 29 | 4-Br-phenyl | -CH₂-(3-I-phenyl) | 0 | H |
| 30 | 4-Br-phenyl | -CH₂-(3-I-phenyl) | 0 | CH₂CH₃ |
| 31 | 4-Br-phenyl | -CH₂-(3-I-phenyl) | 1 | H |

TABLE 1-4

| Compound No. | R¹ | R² | n | X |
|---|---|---|---|---|
| 32 | 4-Br-phenyl-CH₂- | (CH₂)₂CH₃ | 0 | isopropyl |
| 33 | 4-Br-phenyl-CH₂- | (CH₂)₂CH₃ | 0 | isopropyl (stereo) |
| 34 | 4-Br-phenyl-CH₂- | (CH₂)₂CH₃ | 0 | benzyl |
| 35 | 4-Br-phenyl-CH₂- | (CH₂)₂CH₃ | 0 | benzyl (stereo) |
| 36 | 3-I-phenyl-CH₂- | (CH₂)₂CH₃ | 0 | CH₂CH₃ |
| 37 | 2-furyl-CH₂- | (CH₂)₂CH₃ | 0 | H |
| 38 | 2-furyl-CH₂- | (CH₂)₂CH₃ | 0 | CH₂CH₃ |

The pharmacological actions of compounds (I) will be described with reference to test examples.

Test Example 1: Test of Adenosine $A_3$ Receptor Binding

This test was carried out according to the method which was a slightly modified method of Linden et al. (International Application No. WO 95/11681).

The transfected HEK293 cells that expressed the human adenosine $A_3$ receptors were homogenized in 5 mM tris (hydroxymethyl)aminomethane hydrochloric acid buffer containing 5 mM magnesium chloride (pH 7.6) by a Teflon homogenizer (Iuchiseieido Corp.). The resultant suspension was centrifuged (4000×g, 20 minutes), and a 50 mM tris (hydroxymethyl)aminomethane/10 mM magnesium chloride/hydrochloric acid buffer (pH 7.6) (referred to as "the Tris-HCl buffer" hereinafter) was added to the precipitate to generate the cell suspension ( the protein concentration 0.25 mg/ml). To the cell suspension was added adenosine deaminase so that the concentration was 2 U/ml, and the resultant mixture was used in the following binding experiment.

10μl (final concentration 0.1 nM) of $^{125}$I labeled 6-(3-iodo-4-aminobenzyl) adenosine-5'-N-methyluronamide ([$^{125}$I]AB-MECA: 2000 Ci/mmol; Amersham Corp.) and 10 μl of test compound were added to the cell suspension (80 μl). After incubation at 25° C. for 120 minutes, the reaction mixture was rapidly filtered with a glass fiber filter (GF/B; Whatman Corp.) treated with 0.3% polyethyleneimine, and immediately washed with 5 ml of ice-cooled Tris-HCl buffer three times. The glass fiber filter was transferred to a polypropylene tube, and the radioactivity was measured by a gamma counter (Packard Corp.).

The rate of inhibition of adenosine $A_3$ receptor binding ([$^{125}$I]AB-MECA) of a test compound was calculated by the following equation:

$$\text{(Rate of inhibition)} = (A-B)/(C-D) \times 100$$

A: Amount of binding in the presence of the test compound
B: Amount of non-specific binding
C: Amount of total binding
D: Amount of non-specific binding (Note) The amount of total binding means the binding radioactivity of [$^{125}$I]AB-MECA in the absence of a test compound. The amount of non-specific binding means the binding radioactivity of [125I]AB-MECA in the presence of 100 μM $N^6$-[(R)-phenylisopropyl] adenosine (Sigma Corp.) The amount of binding in the presence of a test compound means the binding radioactivity of [125I]AB-MECA binding in the presence of a test compound at each concentration.

The result is shown in Table 2.

TABLE 2

| Compound No. | The rate of inhibition (%) $10^{-8}$M/$10^{-7}$M |
|---|---|
| 1 | 88/97 |
| 2 | 29/55 |
| 3 | 65/96 |
| 4 | 73/90 |
| 5 | 100/100 |
| 6 | 98/100 |
| 8 | 100/96 |
| 13 | 75/76 |
| 14 | 29/55 |
| 15 | 21/66 |
| 16 | 17/92 |
| 17 | 36/70 |
| 25 | 94/97 |
| 26 | 85/100 |
| 32 | 84/120 |
| 33 | 89/95 |
| 35 | 94/52 |

Compounds (I) or pharmacologically acceptable salts thereof exhibited strong adenosine $A_3$ acceptor antagonising activity. Therefore, a medicine containing one of compounds (I) as an effective ingredient is effective for allergic diseases and asthma which are caused by hyperactivity of adenosine $A_3$ acceptors.

Test Example 2: Test of Inhibition of Compound 48/80 Induced Pruritic Action

It is known that compound 48/80 exhibits an pruritic action (European Journal of Pharmacology, Vol. 275, pp 229–233, 1995). A group consisting of 10 ddy mice (Japanese SLC) having a body weight of 10 to 21 g was used in the test. After compound 5 was orally administered, 0.5 mg/kg of compound 48/80 was subcutaneously administered in a volume of 0.1 ml per 20 g. 10 minutes after administration of compound 48/80, the number of scratching behavior was measured for 10 minutes. The rate of inhibition of the group of mice administered with compound 5 relative to the number of scratching behavior of a control group was calculated, and $ED_{50}$ was calculated from the rate of inhibition.

The results are shown in Table 3.

TABLE 3

| Compound | No. of animal | Dose (mg/kg, p.o.) | (A) | (B) | $ED_{50}$ |
|---|---|---|---|---|---|
| Normal Control[a] | 10 | — | 1.60 ± 0.64 | | |
| Positive Control[b] | 10 | — | 16.20 ± 3.56 | | |
| Compound 5 | 10 | 30 | 10.70 ± 4.45 | 34.0% | |
| | 10 | 100 | 7.60 ± 3.12 | 53.1% | 96.8 mg/kg |
| | 10 | 300 | 6.00 ± 2.88 | 63.0% | |

[a]Saline 0.1 mg/kg, s.c.,
[b]Compound 48/80 0.5 mg/kg, s.c
(A): The number of scratching bebavior/10 minutes
(B): The rate of inhibition (%)

Compound 5 exhibited its inhibitory action on the compound 48/80 induced itching.

Test Example 3: Action on Acute Toxicity

A group consisting of three ddY mice (Japanese SLC) having a body weight of 19 to 21 g was used. One week after oral administration of compound 5, death of the mice was observed.

After oral administration of 1000 mg/kg of compound 5, no death was observed in the mice.

Although compounds (I) or pharmacologically acceptable salts thereof can be administered singly, the compounds are preferably provided as medical formulations. Also these medical formations are used for animals and humans.

A pharmaceutical composition according to the present invention can contains, as an active ingredient, compounds (I) or pharmacologically acceptable salts thereof singly or in a mixture with any other active ingredient for different other treatment. Such a medical formulation is produced by any desired method well known in the technical field of pharmaceutics after an active ingredient is mixed with at least one pharmacologically acceptable carrier.

As the administration route, a route which is the most effective for intended treatment is preferably used, and an oral or parenteral route, for example, intraoral, tracheobronchial, intrarectal, subcutaneous, intramuscular or intravenous administration, can be used.

As the administration form, a nebula, a capsule, a tablet, granules, syrup, an emulsion, a suppository, an injection, ointment, a tape, and the like can be used.

Liquid preparations suitable for oral administration, such as an emulsion and syrup, can be produced by using water, sucrose, sorbitol, saccharide such as fructose or the like; glycol such as polyethylene glycol, propylene glycol, or the like; oil such as olive oil, soybean oil, or the like; a preservative such as p-hydroxybenzoate or the like; and flavor such as a strawberry flavor, a peppermint flavor, or the like. A capsule, a tablet, a powder and granules can be produced by using an excipient such as lactose, glucose, sucrose, mannitol, or the like; a disintegrator such as starch, sodium alginate, or the like; a lubricant such as magnesium stearate, talc, or the like; a binder such s polyvinyl alcohol, hydroxypropyl cellulose, gelatin, or the like; a surfactant such as a fatty acid ester or the like; and a plasticizer such as glycerin, or the like.

Formulations suitable for parenteral administration comprise a sterilized aqueous agent containing an active compound which is preferably isotonic to the blood of a recipient person. For example, for an injection, an injection solution is prepared by using a salt solution, a glucose solution or a carrier comprising a mixture of brine and a glucose solution. Formulations for entral administration are prepared by using a carrier, e.g., cacao butter, hydrogenated fat, hydrogenated carboxylic acid, or the like, and provided as suppositories. A nebula is prepared by using an active compound or a carrier which disperses the active compound as fine particles and facilitates absorption without irritating the oral cavity and the airway mucous membrane of a recipient person. Examples of the carrier include lactose, glycerin and the like. Depending upon the properties of the active compound and the carrier used, formulations such as aerosol, dry powder, and the like can be formed.

To these parenteral agents can be added as an auxiliary ingredient at least one selected from glycols, oils, flavors, preservatives, excipients, disintegrators, lubricants, binders, surfactants, and plasticizers, which are examples for oral agents.

Although the effective amount and the number of administrations of compounds (I) or pharmacologically acceptable salts thereof vary depending upon the administration form, the age and body weight of a patient, symptoms to be treated, or severity, 1 to 50 mg/kg is preferably administered in 3 to 4 divided doses per day. However, such a dose varies with the above-described various conditions.

Best Mode for Carrying Out the Invention

Examples, reference examples and formulation examples are described below.

EXAMPLE 1

2-(p-Bromophenyl)-4-ethyl-1,4,7,8-tetrahydro-5H-imidazo[2,1-i]purine-5-one hydrochloride (Compound 1)

3.5 g (9.61 mmol) of compound c obtained in Reference Example 3 was dissolved in 10 ml of dimethyl sulfoxide, and 2.86 ml (48.0 mmol) of ethanolamine was added to the resultant solution, followed by stirring at 150° C. for 2 hours. After the reaction solution was cooled to room temperature, the solution was neutralized by adding water and 2N hydrochloric acid, and the thus-obtained crystals were collected. The crystals were washed with water and then ether, and dried under reduced pressure. To the thus-obtained crystals were added 30 ml of chloroform and 2.8 ml (38.4 mmol) of thionyl chloride, followed by heating under reflux for 2 hours. After the reaction solution was cooled to room temperature, 100 ml of ether was added to the solution, and the thus-precipitated crystals were collected off. The crystals obtained were washed with ether to obtain 3.66 g (yield: 87%) of titled compound 1 as pale yellow crystals.

$^1$H-NMR (DMSO-$d_6$) δ (ppm); 8.04(d, J=8.4 Hz, 2H), 7.83(d, J=8.4 Hz, 2H), 4.36–3.76(m, 6H), 1.30(t, J=6.9 Hz, 3H) MS(m/e); 361, 359($M^+$)

IR(KBr, $cm^{-1}$); 1718, 1682, 1600, 1475 Melting point; >300° C. Elementary analysis; For $C_{15}H_{14}N_5OBr$ 2.1 HCl. Calculated (%): C, 41.25; H, 3.72; N, 16.03. Found (%): C, 41.36; H, 3.47; N, 15.86.

EXAMPLE 2

2-(p-Bromophenyl)-4-ethyl-1,4,5,7,8,9-hexahydropyrimido [2,1-i]purine-5-one hydrochloride (Compound 2)

Example 1 was repeated except that 4.0 g (11.0 mmol) of compound c obtained in Reference Example 3, 4.2 ml (54.6 mmol) of 3-aminopropanol, and 2.3 ml (31.6 mmol) of thionyl chloride were used to obtain 3.52 g (yield: 71%) of titled compound 2 as white crystals.

$^{1}$H-NMR (DMSO-$d_6$) δ (ppm); 8.03(d, J=8.4 Hz, 2H), 7.57(d, J=8.4 Hz, 2H), 4.11(q, J=6.9 Hz, 2H), 3.98–3.89(m, 2H), 3.51–3.40(m, 2H), 2.12–2.01(m, 2H), 1.28(t, J=6.9 Hz, 3H) MS(m/e); 375, 373 (M$^+$)

IR(KBr, cm$^{-1}$); 1682, 1600, 1478, 1418 Melting point; >300° C. Elementary analysis; For $C_{16}H_{16}N_5OBr$ 2.1 HCl. Found (%): C, 42.81; H, 3.93; N, 15.50. Calculated (%): C, 42.63; H, 4.05; N, 15.54.

EXAMPLE 3

2-(p-Bromophenyl)-4-ethyl-8-methyl-1,4,7,8-tetrahydro-5H-imidazo [2,1-i]-purine-5-one hydrochloride (Compound 3)

Example 1 was repeated except that 4.0 g (10.95 mmol) of compound c obtained in Reference Example 3, 4.3 ml (54.8 mmol) of 2-aminopropanol, and 2.1 ml (28.2 mmol) of thionyl chloride were used to obtain 3.92 g (yield: 79%) of titled compound 3 as yellow crystals.

$^{1}$H-NMR (DMSO-$d_6$) δ (ppm); 8.02(d, J=8.4 Hz, 2H), 7.84(d, J=8.4 Hz, 2H), 4.36–4.05(m, 3H), 3.63–3.46(m, 2H), 1.33–1.21(m, 6H) MS(m/e); 375, 373 (M$^+$)

IR(KBr, cm$^{-1}$); 1682, 1658, 1600, 1478, 1418 Melting point; 256.0–259.5° C. Elementary analysis; For $C_{16}H_{16}N_5OBr$ 2.1HCl. Found (%): C, 42.83; H, 4.20; N, 15.41. Calculated (%): C, 42.63; H, 4.05; N, 15.51.

EXAMPLE 4

2-(p-Bromophenyl)-4,8-diethyl-1,4,7,8-tetrahydro-5H-imidazo[2,1-i]purine-5-one hydrochloride (Compound 4)

Example 1 was repeated except that 2.46 g (6.76 mmol) of compound c obtained in Reference Example 3, 3.19 ml (33.8 mmol) of 2-aminobutanol, and 1.5 ml (20.3 mmol) of thionyl chloride were used to obtain 2.53 g (yield: 83%) of titled compound 4 as pale yellow crystals.

$^{1}$H-NMR (DMSO-$d_6$) δ (ppm); 10.05(d(br), J=9.0 Hz, 1H), 8.04(d, J=8.4 Hz, 2H), 7.82(d, J=8.4 Hz, 2H), 4.26–4.16(m, 1H), 4.10(q, J=6.9 Hz; 2H), 3.66–3.47(m, 2H), 1.70–1.53(m, 2H), 1.31(t, J=6.9 Hz, 3H), 0.96(t, J=7.4 Hz, 3H) MS(m/e); 389, 387 (M$^+$)

IR(KBr, cm$^{-1}$); 1718, 1680, 1590, 1475 Melting point; 237.6–238.5° C. Elementary analysis; For $C_{17}H_{18}N_5OBr$ 2.1 HCl. Found (%): C, 43.91; H, 4.74; N, 15.04. Calculated (%): C, 43.93; H, 4.36; N, 15.07.

EXAMPLE 5

2-(p-Bromophenyl)-4-propyl-1,4,7,8-tetrahydro-5H-imidazo [2,1-i]purine-5-one hydrochloride (Compound 5)

Example 1 was repeated except that 10 g (26.4 mmol) of compound f obtained in Reference Example 6, 7.5 ml (132 mmol) of aminoethanol, and 5.36 ml (73.5 mmol) of thionyl chloride were used to obtain 10.0 g (yield: 87%) of titled compound 5 as light brown crystals.

$^{1}$H-NMR (DMSO-$d_6$) δ (ppm); 10.10(s(br), 1H) 8.01(d, J=7.9 Hz, 2H), 7.84(d, J=8.3 Hz, 2H), 4.28–3.81(m, 6H), 1.76(q, J=7.3 Hz, 2H), 0.94(t, J=7.3 Hz, 3H) MS(m/e); 375, 373 (M$^+$)

IR(KBr, cm$^{-1}$); 1705, 1681, 1520, 1182 Melting point; 265.5–268.2° C. Elementary analysis; For $C_{16}H_{16}N_5OBr$ 2.2 HCl. Found (%): C, 42.30; H, 3.89; N, 15.23. Calculated (%): C, 42.29; H, 4.04; N, 15.41.

EXAMPLE 6

2-Bromophenyl)-4-propyl-1,4,7,8-hexahydropyrimido [2,1-i]purine-5-one hydrochloride (Compound 6)

Example 1 was repeated except that 10 g (26.4 mmol) of compound f obtained in Reference Example 6, 10.1 ml (132 mmol) of 3-aminopropanol, and 5.65 ml (77.4 mmol) of thionyl chloride were used to obtain 10.36 g (yield: 84%) of titled compound 6 as white crystals.

$^{1}$H-NMR (DMSO-$d_6$) δ (ppm); 8.03(d, J=7.9 Hz, 2H), 7.84(d, J=8.2 Hz, 2H) 4.12–3.30(m, 2H), 3.84–3.30(m, 4H), 2.20–2.08(m, 2H), 1.81–1.70(m, 2H), 0.94(t, J=7.3 Hz, 3H) MS(m/e); 389, 387 (M$^+$)

IR(KBr, cm$^{-1}$); 1678, 1600, 1468, 1418 Melting point; >300° C. Elementary analysis; For $C_{17}H_{18}N_5OBr$ 2.2 HCl. Found (%): C, 43.63; H, 4.20; N, 14.88. Calculated (%): C, 43.59; H, 4.35; N, 14.95.

EXAMPLE 7

2- (p-Bromophenyl)-8-methyl-4-propyl-1,4,7,8-tetrahydro-5H-imidazo[2,1-i]purine-5-one hydrochloride (Compound 7)

Example 1 was repeated except that 2 g (5.29 mmol) of compound f obtained in Reference Example 6, 2.11 ml (26.5 mmol) of 2-aminopropanol, and 1.59 ml (21.85 mmol) of thionyl chloride were used to obtain 1.58 g (yield: 64%) of titled compound 7 as yellow crystals.

$^{1}$H-NMR (DMSO-$d_6$) δ (ppm); 8.10–8.00(m, 2H), 7.83(d, J=6.9 Hz, 2H), 4.40–3.70(m, 5H), 1.76(q, J=6.9 Hz, 2H), 1.40(t, J=6.4 Hz, 3H), 0.94(t, J=7.4 Hz, 3H) MS(m/e); 389, 387 (M$^+$)

IR(KBr, cm$^{-1}$); 2970, 1680, 1600, 1475 Melting point; 265.5–267.5° C. Elementary analysis; For $C_{18}H_{18}N_5OBr$ 1.9 HCl. Found (%): C, 46.27; H, 4.68; N, 14.67. Calculated (%): C, 46.04; H, 4.27; N, 14.91.

EXAMPLE 8

2-(p-Bromophenyl)-8-ethyl-4-propyl-1,4,7,8-tetrahydro-5H-imidazo[2,1-i]purine-5-one hydrochloride (Compound 8)

Example 1 was repeated except that 10 g (26.4 mmol) of compound f obtained in Reference Example 6, 12.47 ml (132 mmol) of 2-aminobutanol, and 5.17 ml (70.9 mmol) of thionyl chloride were used, to obtain 9.57 g (yield: 77%) of titled compound 8 as yellow crystals.

$^{1}$H-NMR (DMSO-$d_6$) δ (ppm); 8.04(d, J=8.3 Hz, 2H), 7.84(d, J=8.6 Hz, 2H), 4.52–4.30(m, 1H), 4.13–3.72(m, 4H), 1.85–1.68(m, 4H), 1.03–0.91(m, 6H) MS(m/e); 339 (M$^+$)

IR(KBr, cm$^{-1}$); 1715, 1675, 1600, 1475, 1418 Melting point; 255.5–258.5° C. Elementary analysis; For $C_{18}H_{20}N_5OBr$ 2 HCl. Found (%): C, 45.47; H, 4.80; N, 14.60. Calculated (%): C, 45.49; H, 4.67; N, 14.47.

EXAMPLE 9

2-(o-Bromophenyl)-4-propyl-1,4,7,8-tetrahydro-5H-imidazo [2,1-i]purine-5-one hydrochloride (Compound 9)

Example 1 was repeated except that 3.0 g (7.94 mmol) of compound i obtained in Reference Example 9, 2.39 ml (39.7 mmol) of aminoethanol, and 2.27 ml (31.1 mmol) of thionyl chloride were used, to obtain 2.53 g (yield: 65%) of titled compound 9 as white crystals.

$^1$H-NMR (DMSO-d$_6$) δ (ppm); 7.88–7.75(m, 2H), 7.64–7.52(m, 2H), 4.08–3.83(m, 6H), 1.79–1.68(m, 2H), 0.93(t, J=7.4 Hz, 3H) MS(m/e); 375, 373 (M$^+$)

IR(KBr, cm$^{-1}$); 1718, 1677, 1627, 1571 Melting point; 180.2–180.7° C. Elementary analysis; For C$_{16}$H$_{16}$N$_5$OBr 2.0 HCl. Found (%): C, 43.20; H, 4.13; N, 15.47. Calculated (%): C, 42.98; H, 4.06; N, 15.66.

EXAMPLE 10

4-Propyl-2-(p-tolyl)-1,4,7,8-tetrahydro-5H-imidazo [2,1-i]purine-5-one hydrochloride (Compound 10)

Example 1 was repeated except that 1.2 g (3.82 mmol) of compound m obtained in Reference Example 12, 1.13 ml (19.1 mmol) of aminoethanol, and 3 ml (41.1 mmol) of thionyl chloride were used, to obtain 1.07 g (yield: 73%) of titled compound 10 as brown crystals.

$^1$H-NMR (DMSO-d$_6$) δ (ppm); 8.03–7.97(m, 2H), 7.42(d, J=7.9 Hz, 2H), 4.20–3.85(m, 6H), 2.40(s, 3H), 1.77(q, J=7.4 Hz, 2H), 0.94(t, J=7.4 Hz, 3H) MS(m/e); 309 (M$^+$)

IR(KBr, cm$^{-1}$); 2724, 1548, 1463, 1440 Melting point; >300° C. Elementary analysis; For C$_{17}$H$_{19}$N$_5$O$_{2.1}$ HCl. Found (%): C, 53.07; H, 5.57; N, 17.95. Calculated (%): C, 52.91; H, 5.51; N, 18.15.

EXAMPLE 11

2-(o-Bromophenyl)-8-ethyl-4-propyl-1,4,7,8-tetrahydro-5H-imidazo[2,1-i]purine-5-one hydrochloride (Compound 11)

Example 1 was repeated except that 2.0 g (5.29 mmol) of compound i obtained in Reference Example 9, 2.50 ml (26.5 mmol) of 2-aminobutanol, and 1.63 ml (22.3 mmol) of thionyl chloride were used, to obtain 1.64 g (yield: 64%) of titled compound 11 as white crystals.

$^1$H-NMR (DMSO-d$_6$) δ (ppm); 7.89–7.75(m, 2H), 7.65–7.50(m, 2H), 4.51–4.34(m, 2H), 4.08–3.73(m, 3H), 1.81–1.68(m, 4H), 1.07–0.90(m, 6H) MS(m/e); 403, 401 (M$^+$)

IR(KBr, cm$^{-1}$); 1702, 1672, 1623, 1540 Melting point; 160.0–161.0° C. Elementary analysis; For C$_{18}$H$_{20}$N$_5$OBr 2.3 HCl. Found (%): C, 44.25; H, 4.41; N, 14.76. Calculated (%): C, 44.47; H, 4.62; N, 14.41.

EXAMPLE 12

8-Ethyl-4-propyl-2-(p-tolyl)-1,4,7,8-tetrahydro-5H-imidazo[2.1-i]purine-5-one hydrochloride (Compound 12)

Example 1 was repeated except that 1.2 g (3.82 mmol) of compound m obtained in Reference Example 12, 1.81 ml (19.1 mmol) of 2-aminobutanol, and 3.0 ml (41.1 mmol) of thionyl chloride were used, to obtain 0.24 g (yield: 52%) of titled compound 12 as white crystals.

$^1$H-NMR (DMSO-d$_6$) δ (ppm); 8.01(d, J=7.2 Hz, 2H), 7.42(d, J=7.9 Hz, 2H), 4.54–4.37(m, 1H), 4.16–3.75(m, 4H), 2.40(s, 3H), 1.82–1.73(m 4H), 1.02–0.92(m 6H) MS(m/e); 337 (M$^+$)

IR(KBr, cm$^{-1}$); 1716, 1635, 1621, 1567 Melting point; 169.8–170.2° C. Elementary analysis; For C$_{19}$H$_{23}$N$_5$O 2.3 HCl. Found (%): C, 54.46; H, 6.16; N, 16.28. Calculated (%): C, 54.17; H, 6.05; N, 16.62.

EXAMPLE 13

Ethyl (E)-4-(4-ethyl-1,4,7,8-tetrahydro-5H-imidazo [2,1-i]purine-5-one-2-yl)cinnamate (Compound 13)

3.66 g (8.47 mmol) of compound 1 obtained in Example 1 was suspended in 50 ml of tetrahydrofuran, and 7.1 ml (50.8 mmol) of triethylamine and 4.5 ml (25.4 mmol) of 2-(chloromethoxy)ethyl trimethylsilane were added to the resultant suspension, followed by stirring at room temperature overnight. After the solvent was distilled off, chloroform and water were added to the residue to extract an organic layer. The thus-obtained organic layer was dried over anhydrous magnesium sulfate, and the solvent was distilled off, followed by purification by silica gel column chromatography (eluting solvent: 40% ethyl acetate-hexane) to obtain 1.44 g (yield; 35%) of main product.

1.44 g (2.94 mmol) of the thus-obtained main product was dissolved in 5 ml of dimethylformamide, and 4.1 ml (29.4 mmol) of triethylamine, 3.13 ml (29.4 mmol) of ethyl acrylate and 103 mg (0.15 mmol) of dichlorobistriphenylphosphine palladium were added to the resultant solution, followed by stirring at 100° C. for 8 hours. After the reaction solution was cooled to room temperature, chloroform and water were added to the reaction mixture to extract an organic layer. The thus-obtained organic layer was dried over anhydrous magnesium sulfate, and the solvent was distilled off, followed by purification by silica gel column chromatography (eluting solvent: 40% ethyl acetate-hexane) to obtain 890 mg (yield: 59%) of main product.

To 1.0 g (1.96 mmol) of the main product were added 15 ml of ethanol and 10 ml of 2N hydrochloric acid, followed by heating under reflux for 2 hours. After the reaction solution was cooled to room temperature, the solution was neutralized with a 2N sodium hydroxide aqueous solution, and the precipitated crystals were collected. The crystals obtained were purified by silica gel column chromatography (eluting solvent: 2% methanol-chloroform), and then recrystallized from ethanol to obtain 520 mg (total yield: 14%) of titled compound 13 as white crystals.

$^1$H-NMR (CDCl$_3$) δ (ppm); 8.18(d, J=8.4 Hz, 2H), 7.70(d, J=16.3 Hz, 1H), 7.58(d, J=8.4 Hz, 2H), 6.47(d, J=15.8 Hz, 1H), 4.34–4.15(m, 6H), 3.66(t, J=8.9 Hz, 2H), 1.43(t, J=6.9 Hz, 3H), 1.35(t, J=7.4 Hz, 3H) MS(m/e); 379 (M$^+$)

IR(KBr, cm$^{-1}$); 1720, 1648, 1541, 1455 Melting point; 261.0–269.5° C. Elementary analysis; For C$_{20}$H$_{21}$N$_5$O$_3$ 0.5H$_2$O. Found (%): C, 61.90; H, 5.79; N, 17.74. Calculated (%): C, 61.84; H, 5.71; N, 18.03.

EXAMPLE 14

Ethyl (E)-4-(4-ethyl-1,4,5,7,8,9-hexahydropyrimido [2,1-i]purine-5-one-2-yl)cinnamate (Compound 14)

2.11 g (4.72 mmol) of compound 2 obtained in Example 2 was suspended in 50 ml of tetrahydrofuran, and 2.6 ml (18.9 mmol) of triethylamine and 1.6 ml (9.44 mmol) of 2-(chloromethoxy)ethyl trimethylsilane were added to the resultant suspension, followed by stirring at room temperature overnight. After the solvent was distilled off, ethyl acetate and water were added to the residue to extract an organic layer. The thus-obtained organic layer was dried over anhydrous magnesium sulfate, and the solvent was distilled off, followed by purification by silica gel column chromatography (eluting solvent: 30% ethyl acetate-hexane) to obtain 2.11 g (yield: 89%) of a main product.

2.11 g (4.20 mmol) of the thus-obtained main product was dissolved in 5 ml of dimethylformamide, and 5.85 ml (42 mmol) of triethylamine, 4.46 ml (42 mmol) of ethyl acrylate 150 mg (0.21 mmol) of dichlorobistriphenylphosphine palladium were added to the resultant solution, followed by stirring at 100° C. for 8 hours. After the reaction solution was cooled to room temperature, chloroform and water were added to the reaction solution to extract an organic layer. The thus-obtained organic layer was dried over anhydrous magnesium sulfate, and the solvent was distilled off, followed by purification by silica gel column chromatography (eluting solvent: 40% ethyl acetate-hexane) to obtain 1.54 mg (yield: 70%) of a main product.

To 1.67 g (3.19 mmol) of the product were added 15 ml of tetrahydrofuran and 14.7 ml of a solution of 1M tetrabutylammonium fluoride in tetrahydrofuran, followed by heating under reflux for 6 hours. After the reaction solution was cooled to room temperature, an ammonium acetate aqueous solution and chloroform were added to the solution to extract an organic layer. The thus-obtained organic layer was washed with saturated saline, and dried over anhydrous magnesium sulfate. After the solvent was distilled off, the residue was purified by silica gel column chromatography (eluting solvent: 2% ethanol-chloroform) to obtain 720 mg (total yield: 36%) of titled compound 14.

$^1$H-NMR (DMSO-$d_6$) δ (ppm); 8.18(d, J=8.4 Hz, 2H), 7.87(d, J=8.4 Hz, 2H), 7.68(d, J=15.8 Hz, 1H), 6.73(d, J=15.8 Hz, 1H), 4.25–4.10(m, 4H), 3.99(t, J=6.9 Hz, 2H), 2.82(t, J=7.9 Hz, 2H), 1.99–1.85(m, 2H), 1.33–1.24(m, 6H) MS(m/e); 393 (M$^+$)

EXAMPLE 15

(E)-4-(4-Ethyl-1,4,5,7,8, 9-hexahydropyrimido [2,1-i]-purine-5-one-2-yl)cinnamic acid (Compound 15)

480 mg (1.22 mmol) of compound 14 obtained in Example 14 was suspended in 10 ml of ethanol, and 10 ml of 2N sodium hydroxide aqueous solution was added to the resultant suspension, followed by stirring at room temperature for 4 hours. The mixture was then neutralized with 2N hydrochloric acid, and the precipitated crystals were collected off, washed with water, and then recrystallized from dimethylsulfoxide-water to obtain 112 mg (yield: 25%) of titled compound 15 as yellow crystals.

$^1$H-NMR (DMSO-$d_6$) δ (ppm); 8.31(d, J=8.2 Hz, 2H), 7.68(d, J=8.4 Hz, 2H), 7.59(d, J=16.2 Hz, 1H), 6.49(d, J=15.8 Hz, 1H), 4.12(q, J=6.9 Hz, 2H), 4.00–3.93(m, 2H), 3.45–3.25(m, 2H), 2.11–2.00(m, 2H), 1.29(t, J=6.9 Hz 3H) MS(m/e); 379 (M$^+$)

IR(KBr, cm$^{-1}$); 2970, 1715, 1660, 1380 Melting point; >300° C. Elementary analysis; For $C_{19}H_{19}N_5O_3$ 1.5$H_2O$. Found (%): C, 58.23; H, 5.40; N, 17.63. Calculated (%): C, 58.16; H, 5.65; N, 17.85.

EXAMPLE 16

Ethyl (E)-4-(4,8-diethyl-1,4,7,8-tetrahydro-5H-imidazo-[2,1-i]purine-5-one-2-yl)cinnamate (Compound 16)

5.5 g (11.9 mmol) of compound 4 obtained in Example 4 was suspended in 30 ml of dimethylformamide, and 8.31 ml (59.7 mmol) of triethylamine and 4.22 ml (23.9 mmol) of 2-(chloromethoxy)ethyl trimethylsilane were added to the resultant suspension, followed by stirring at room temperature for 3 hours. To the reaction solution were added chloroform and water to extract an organic layer. The thus-obtained organic layer was dried over anhydrous magnesium sulfate, and the solvent was distilled off, followed by purification by silica gel column chromatography (eluting solvent: 20% ethyl acetate-hexane for the first fraction, 30% ethyl acetate-hexane for the second fraction) to obtain 2.08 g (total yield of the first and second fractions; 34%) of a main product.

590 mg (1.14 mmol) of the thus-obtained main product (first fraction) was dissolved in 5 ml of dimethylformamide, and 1.59 ml (11.4 mmol) of triethylamine, 1.21 ml (11.4 mmol) of ethyl acrylate and 40 mg (0.06 mmol) of dichlorobistriphenylphosphine palladium were added to the resultant solution, followed by stirring at 100° C. for 8 hours. After the reaction solution was cooled to room temperature, chloroform and water were added to the reaction solution to extract an organic layer. The thus-obtained organic layer was dried over anhydrous magnesium sulfate, and the solvent was distilled off, followed by purification by silica gel column chromatography (eluting solvent: 30% ethyl acetate-hexane) to obtain 480 mg (yield: 78%) of a main product. 866 mg (yield: 58%) of the main product was obtained from 1.43 mg (2.76 mmol) of the second fraction by the same operation.

To 440 mg (1.82 mmol) of the product (obtained from the first fraction) were added 3 ml of tetrahydrofuran and 4.1 ml of a solution of 1M tetrabutylammonium fluoride in tetrahydrofuran, followed by heating under reflux for 4 hours.

After the reaction solution was cooled to room temperature, an ammonium acetate aqueous solution and chloroform were added to the solution to extract an organic layer. The thus-obtained organic layer was washed with saturated brine, and dried over anhydrous magnesium sulfate. After the solvent was distilled off, the residue was purified by silica gel column chromatography (eluting solvent: 2% methanol-chloroform) to obtain 220 mg of a main product. 490 mg of main product was obtained from 760 mg (1.4 mmol) of a main product obtained from the second fraction by the same operation as the above. Both of the thus obtained both main products were mixed, and 20 ml of chloroform and 10 ml of 1N hydrochloric acid were added to the mixture, followed by vigorous stirring at room temperature for 2 hours. The organic layer was washed with water and dried over anhydrous magnesium sulfate, and the solvent was distilled off under reduced pressure to obtain 590 mg (total yield: 14%) of titled compound 16.

$^1$H-NMR (CDCl$_3$) δ (ppm); 11.31(br(s), 1H), 8.17(d, J=8.4 Hz, 2H), 7.70(d, J=14.8 Hz, 1H), 7.66(d, J=7.9 Hz, 2H), 6.52(d, J=15.8 Hz, 1H), 4.49–4.40(m, 2H), 4.33–4.25 (m, 4H), 4.05–3.95(m, 1H), 1.94–1.76(m, 2H), 1.43(t, J=6.9 Hz, 3H), 1.36(t, J=7.4 Hz, 3H), 1.15(t, J=7.4 Hz, 3H) MS(m/e); 407 (M$^+$)

EXAMPLE 17

(E)-4-(4,8-Diethyl-1,4,7,8-tetrahydro-5H-imidazo [2,1-i]-purine-5-one-2-yl)cinnamic acid (Compound 17)

Example 15 was repeated except that 660 mg (1.62 mmol) of compound 16 obtained in Example 16 was used to obtain 345 mg (yield: 56%) of titled compound 17 as yellow crystals.

$^1$H-NMR (DMSO-$d_6$) δ (ppm); 8.12(d, J=7.9 Hz, 2H), 7.77(d, J=8.4 Hz, 2H), 7.61(d, J=16.3 Hz, 1H), 6.56(d, J=15.8 Hz, 1H), 4.33–4.26(m, 2H), 4.16–4.07(m, 2H), 3.87–3.73(m, 1H), 1.78–1.63(m, 2H), 1.29(t, J=6.9 Hz, 3H), 0.96(t, J=7.4 Hz, 3H) MS(m/e); 379 (M$^+$)

IR(KBr, cm$^{-1}$); 2940, 1715, 1675, 1580 Melting point; >300° C. Elementary analysis; For $C_{20}H_{21}N_5O_3$ 1.1$H_2O$.

Found (%): C, 60.24; H, 5.72; N, 17.21. Calculated (%): C, 60.17; H, 5.86; N, 17.54.

EXAMPLE 18

Ethyl (E)-4-(4-propyl-1,4,7,8-tetrahydro-5H-imidazo-[2,1-i]purine-5-one-2-yl) cinnamate (Compound 18)

9.36 g (21 mmol) of compound 5 obtained in Example 5 was suspended in 80 ml of tetrahydrofuran, and 17.6 ml (126 mmol) of triethylamine and 11.2 ml (63 mmol) of 2-(chloromethoxy)ethyl trimethylsilane were added to the resultant suspension, followed by stirring at room temperature overnight. To the reaction solution were added ethyl acetate and water to extract an organic layer. The thus-obtained organic layer was washed with saturated brine and dried over anhydrous magnesium sulfate, and the solvent was distilled off, followed by purification by silica gel column chromatography (eluting solvent: 30% ethyl acetate-hexane for the first fraction, 50% ethyl acetate-hexane for the second fraction) to obtain 3.31 g (total yield of the first and second fractions; 31%) of a main product.

900 mg (1.78 mmol) of the thus-obtained main product (first fraction) was dissolved in 5 ml of dimethylformamide, and 2.49 ml (17.85 mmol) of triethylamine, 1.90 ml (17.85 mmol) of ethyl acrylate and 60 mg (0.09 mmol) of dichlorobistriphenylphosphine palladium were added to the resultant solution, followed by stirring at 100° C. for 5 hours. After the reaction solution was cooled to room temperature, chloroform and water were added to the reaction solution to extract an organic layer. The thus-obtained organic layer was dried over anhydrous magnesium sulfate, and the solvent was distilled off, followed by purification by silica gel column chromatography (eluting solvent: 30% ethyl acetate-hexane) to obtain 720 mg (yield: 78%) of a main product.

To 690 mg (1.32 mmol) of the product (obtained from the first fraction) were added 15 ml of ethanol and 15 ml of 1N hydrochloric acid, followed by heating under reflux for 2 hours. After the reaction solution was cooled to room temperature, the solution was neutralized with 2N sodium hydroxide aqueous solution, and the precipitated crystals were filtered off. The crystals obtained were washed with water and then dried to obtain 480 mg (total yield: 22%) of titled compound 18.

$^1$H-NMR (DMSO-$d_6$) δ (ppm); 8.13(d, J=8.5 Hz, 2H), 7.93(d, J=8.6 Hz, 2H), 7.70(d, J=16.2 Hz, 1H), 6.76(d, J=16.2 Hz, 1H), 4.25–4.17(m, 4H), 4.11–4.01(m, 4H), 1.77 (q, J=7.3 Hz, 2H), 1.28(t, J=7.3 Hz, 3H), 0.94(t, J=7.3 Hz, 3H) MS(m/e); 393 (M$^+$)

EXAMPLE 19

(E)-4-(4-Propyl-1,4,7,8-tetrahydro-5H-imidazo [2,1-i]-purine-5-one-2-yl)cinnamic acid (Compound 19)

Example 15 was repeated except that 450 mg (1.14 mmol) of compound 18 obtained in Example 18 was used to obtain 110 mg (yield: 26%) of titled compound 19 as yellow crystals.

$^1$H-NMR (DMSO-$d_6$) δ (ppm); 8.12(d, J=8.2 Hz, 2H), 7.71(d, J=8.2 Hz, 2H), 7.60(d, J=15.8 Hz, 1H), 6.52(d, J=15.8 Hz, 1H), 4.15(t, J=7.9 Hz, 2H), 4.03(t, J=6.6 Hz, 2H), 3.90(t, J=9.9 Hz, 2H), 1.77(q, J=7.6 Hz, 2H), 0.93(t, J=7.6 Hz, 3H) MS(m/e); 366 (M$^+$)

IR(KBr, cm$^{-1}$); 2960, 1705, 1580, 1422 Melting point; >300° C. Elementary analysis; For $C_{19}H_{19}N_5O_3$ 0.6H$_2$O. Found (%): C, 60.56; H, 5.32; N, 18.48. Calculated (%): C, 60.66; H, 5.41; N, 18.62.

EXAMPLE 20

Ethyl (E)-4-(8-Ethyl-4-propyl-1,4,7,8-tetrahydro-5H-imidazo [2,1-i]purine-5-one-2-yl)cinnamate (Compound 20)

Example 14 was repeated except that 9.57 g (20.2 mmol) of compound 8 obtained in Example 8 was used to obtain 1.91 g (yield: 23%) of titled compound 20.

$^1$H-NMR (CDCl$_3$) δ (ppm); 8.17(d, J=8.3 Hz, 2H), 7.70(d, J=15.8 Hz, 1H), 7.62(d, J=8.3 Hz, 2H), 6.50(d, J=16.2 Hz, 1H), 4.42–4.14(m, 6H), 3.95–3.88(m, 1H), 1.88(q, J=7.6 Hz, 2H), 1.74–1.68(m, 2H), 1.35(t, J=7.3 Hz, 3H), 1.03(t, J=7.3 Hz, 3H), 0.97(t, J=7.3 Hz, 3H) MS(m/e); 421 (M$^+$)

EXAMPLE 21

(E)-4-(8-Ethyl-4-propyl-1,4,7,8-tetrahydro-5H-imidazo-[2,1-i]purine-5-one-2-yl)cinnamic acid (Compound 21)

Example 15 was repeated except that 1.52 g (3.62 mmol) of compound 20 obtained in Example 20 was used to obtain 720 mg (yield: 52%) of titled compound 21 as yellow crystals.

$^1$H-NMR (DMSO-$d_6$) δ (ppm); 8.12(d, J=8.2 Hz, 2H), 7.70(d, J=8.3 Hz, 2H), 7.60(d, J=15.8 Hz, 1H), 6.51(d, J=16.2 Hz, 1H), 4.30–4.14(m, 2H), 4.03(t, J=6.6 Hz, 2H), 3.79(q, J=5.0 Hz, 1H), 1.79(q, J=5.0 Hz, 2H), 1.83–1.66(m, 2H), 0.99–0.88(m, 6H) MS(m/e); 392 (M$^+$)

IR(KBr, cm$^{-1}$); 2960, 1715, 1580, 1375 Melting point; >300° C. Elementary analysis. Found (%): C, 61.58; H, 5.84; N, 17.28. Calculated (%): C, 61.57; H, 6.10; N, 17.10.

EXAMPLE 22

2-(m-Bromophenyl)-4-propyl-1,4,7,8-tetrahydro-5H-imidazo [2,1-i]purine-5-one hydrochloride (Compound 22)

Example 1 was repeated except that 2.0 g (5.29 mmol) of compound o obtained in Reference Example 13, 1.57 ml (26.5 mmol) of 2-aminoethanol, and 2.93 ml (40.2 mmol) of thionyl chloride were used to obtain 1.53 g (yield: 78%) of titled compound 22 as a white solid.

$^1$H-NMR (DMSO-$d_6$) δ (ppm) ; 10.45s(br), 1H), 8.26s (br), 1H), 8.11(d, J=7.9 Hz, 1H), 7.79(d, J=7.9 Hz, 1H), 7.57(t, J=7.9 Hz, 1H), 4.40–3.84(m, 6H), 1.77(q, J=7.4 Hz, 2H), 0.95(t, J=7.4 Hz, 3H) MS(m/e); 375, 373 (M$^+$)

IR(KBr, cm$^{-1}$); 1706, 1687, 1656, 1565, 1274 Melting point; 290.5–292.0° C. Elementary analysis; For $C_{16}H_{16}N_5$OBr 2.4 HCl. Found (%): C, 41.58; H, 3.91; N, 14.83. Calculated (%): C, 41.62; H, 4.02; N, 15.17.

EXAMPLE 23

2-(m-Bromophenyl)-8-ethyl-4-propyl-1,4,7,8-tetrahydro-5H-imidazo[2,1-i]purine-5-one hydrochloride (Compound 23)

Example 1 was repeated except that 1.5 g (3.97 mmol) of compound o obtained in Reference Example 13, 1.87 ml (19.9 mmol) of 2-aminobutanol, and 2.41 ml (33.0 mmol) of thionyl chloride were used to obtain 1.2 g (yield: 65%) of titled compound 23 as a yellow solid.

$^1$H-NMR (DMSO-$d_6$) δ (ppm); 10.24s(br), 1H), 8.27s(br), 1H), 8.10(d, J=7.9 Hz, 1H), 7.79(d, J=7.9 Hz, 1H), 7.57(t, J=7.9 Hz, 1H), 4.41–3.75(m, 5H), 1.82–1.69(m, 4H), 1.13–0.92(m, 6H) MS(m/e); 403, 401 (M$^+$)

IR(KBr, cm$^{-1}$); 1728, 1693, 1664, 1465 Melting point; 256.5–257.0° C. Elementary analysis; For $C_{18}H_{20}N_5OBr$ 1.7 HCl. Calculated value (%): C, 46.81; H, 4.69; N, 14.78. Measured value (%): C, 46.57; H, 4.71; N, 15.08.

EXAMPLE 24

8-Ethyl-2-phenyl-4-propyl-1,4,7,8-tetrahydro-5H-imidazo[2,1-i]purine-5-one (Compound 24)

Example 1 was repeated except that 1.2 g (4.0 mmol) of compound p obtained in Reference Example 14, 1.9 ml (20.0 mmol) of 2-aminobutanol, and 1.6 ml (21.8 mmol) of thionyl chloride were used to obtain a hydrochloride of titled compound 24. To the thus-obtained hydrochloride were added chloroform and a 1N sodium hydroxide aqueous solution to extract an organic layer. The organic layer was dried over anhydrous magnesium sulfate, and the solvent was distilled off under reduced pressure, followed by recrystallization from ethanol to obtain 0.68 g (yield: 53%) of titled compound 24 as a white solid.

$^1$H-NMR (DMSO-$_6$) δ (ppm); 10.40s(br), 1H), 8.13–8.11 (m, 2H), 7.61–7.54(m, 3H), 4.55–3.75(m, 5H), 1.79–1.73 (m, 4H), 1.06–0.89(m, 6H) MS(m/e); 323 (M$^+$)

IR(KBr, cm$^{-1}$); 1704, 1687, 1683, 1558 Melting point; 262.8–263.5° C. Elementary analysis; For $C_{18}H_{20}N_5O$ 0.4H$_2$O. Found (%): C, 65.49; H, 6.55; N, 21.26. Calculated (%): C, 65.60; H, 6.36; N, 21.25.

EXAMPLE 25

2-(p-Bromophenyl)-8-ethyl-4-methyl-1,4,7,8-tetrahydro-5H-imidazo[2,1-i]purine-5-one hydrochloride (Compound 25)

Example 1 was repeated except that 1.3 g (3.71 mmol) of compound q obtained in Reference Example 15, 1.75 ml (18.6 mmol) of 2-aminobutanol, and 4.0 ml (54.5 mmol) of thionyl chloride were used to obtain 0.56 g (yield: 34%) of titled compound 25 as a pale brown solid.

$^1$H-NMR (DMSO-d$_6$) δ (ppm); 8.02(d, J=8.4 Hz, 2H), 7.81(d, J=8.4 Hz, 2H), 4.43–4.29(m, 2H), 3.94–3.85(m, 1H), 3.51(s, 3H), 1.79–1.69(m, 2H), 0.98(t, J=6.9 Hz, 3H) MS(m/e); 375, 373 (M$^+$)

IR(KBr, cm$^{-1}$); 1716, 1704, 1700, 1596

IR(KBr, cm$^{-1}$); 1716, 1704, 1700, 1596 Melting point; >295° C. Elementary analysis; For $C_{16}H_{16}N_5OBr$ 1.4H$_2$O 1.8 HCl. Found (%): C, 41.43; H, 4.47; N, 14.86. Calculated (%): C, 41.32; H, 4.46; N, 15.06.

EXAMPLE 26

2-(p-Bromophenyl)-4-n-butyl-1,4,7,8-tetrahydro-5H-imidazo[2,1-i]purine-5-one hydrochloride (Compound 26)

Example 1 was repeated except that 2.0 g (5.13 mmol) of compound r obtained in Reference Example 16, 1.52 ml (25.6 mmol) of 2-aminoethanol, and 1.62 ml (22.2 mmol) of thionyl chloride were used to obtain 1.29 g (yield: 63%) of titled compound 26 as a white solid.

$^1$H-NMR (DMSO-d$_6$) δ (ppm); 9.97s(br), 1H), 8.02(d, J=8.9 Hz, 2H), 7.58(d, J=8.9 Hz, 2H), 4.17–3.85(m, 6H), 1.77–1.66(m, 2H), 1.41–1.27(m, 2H), 0.93(t, J=7.4 Hz, 3H) MS(m/e); 389, 387 (M$^+$)

IR(KBr, cm$^{-1}$); 1679, 1670, 1602, 1469, 1411 Melting point; >300° C. Elementary analysis; For $C_{17}H_{18}N_5OBr$ 2.0 HCl. Found (%): C, 44.55; H, 4.43; N, 14.93. Calculated (%): C, 44.27; H, 4.37; N, 15.19.

EXAMPLE 27

2-(p-Bromophenyl)-4-n-butyl-8-ethyl-1,4,7,8-tetrahydro-5H-imidazo[2,1-i]purine-5-one (Compound 27)

Example 1 was repeated except that 2.0 g (5.13 mmol) of compound r obtained in Reference Example 16, 2.04 ml (25.6 mmol) of 2-aminobutanol, and 1.62 ml (22.2 mmol) of thionyl chloride were used to obtain 1.76 g (yield: 71%) of hydrochloride of titled compound 27. To the thus-obtained hydrochloride were added chloroform and a 1N sodium hydroxide aqueous solution to extract an organic layer. The organic layer was dried over anhydrous magnesium sulfate, and the solvent was distilled off under reduced pressure, followed by recrystallization from ethanol to obtain 0.89 g (yield: 41%) of titled compound 27 as a brown solid.

$^1$H-NMR (DMSO-d$_6$) δ (ppm); 10.34s(br), 1H), 8.02(d, J=8.4 Hz, 2H), 7.60(d, J=8.4 Hz, 2H), 4.30–4.15(m, 2H), 4.06(t, J=6.9 Hz, 2H), 3.82–3.72(m, 1H), 1.77–1.63(m, 4H), 1.41–1.27(m, 2H), 0.98–0.90(m, 6H) MS(m/e); 417, 415 (M$^+$)

IR(KBr, cm$^{-1}$); 1704, 1691, 1664, 1544, 1263 Melting point; 268.7–269.7° C. Elementary analysis; For $C_{19}H_{22}N_5OBr$ 0.4H$_2$O. Found (%): C, 54.00; H, 5.38; N, 16.17. Calculated (%): C, 53.88; H, 5.43; N, 16.54.

EXAMPLE 28

2-(p-Bromophenyl)-8-ethyl-4-phenyl-1,4,7,8-tetrahydro-5H-imidazo[2,1-i]purine-5-one hydrochloride (Compound 28)

Example 1 was repeated except that 2.0 g (4.85 mmol) of compound s obtained in Reference Example 17, 2.3 ml (24.3 mmol) of 2-aminobutanol, and 1.62 ml (22.2 mmol) of thionyl chloride were used to obtain 1.0 g (yield: 41%) of titled compound 28 as a white solid.

$^1$H-NMR (DMSO-d$_6$) δ (ppm); 7.89–7.75(m, 4H), 7.60–7.54(m, 5H), 4.35–3.50(m, 3H), 1.85–1.63(m, 2H), 1.01–0.95(m, 3H) MS(m/e); 435 (M$^+$)

IR(KBr, cm$^{-1}$); 1716, 1670, 1587 Melting point; >300° C. Elementary analysis; For $C_{21}H_{18}N_5OBr$ 1.9 HCl. Found (%): C, 50.06; H, 4.18; N, 13.85. Calculated (%): C, 49.89; H, 3.97; N, 13.85.

EXAMPLE 29

2-(p-Bromophenyl)-4-(3-iodobenzyl)-1,4,7,8-tetrahydro-5H-imidazo[2,1-i]purine-5-one hydrochloride (Compound 29)

Example 1 was repeated except that 0.6 g (1.08 mmol) of compound t obtained in Reference Example 18, 0.32 ml (5.42 mmol) of 2-aminoethanol, and 0.33 ml (4.5 mmol) of thionyl chloride were used to obtain 0.22 g (yield: 33%) of titled compound 29 as a brown solid.

$^1$H-NMR (DMSO-d$_6$) δ (ppm); 10.19s(br), 1H), 8.03–7.65(m, 5H), 7.43(d, J=7.3 Hz, 1H), 7.16(t, J=7.3 Hz, 1H), 5.23(s, 2H), 4.27–3.72(m, 4H) MS(m/e); 549, 547 (M$^+$)

IR(KBr, cm$^{-1}$); 1716, 1673, 1602, 1471 Melting point; >263.5–266.2° C.

EXAMPLE 30

2-(p-Bromophenyl)-8-ethyl-4-(3-iodobenzyl)-1,4,7, 8-tetrahydro-5H-imidazo[2,1-i]purine-5-one hydrochloride (Compound 30)

Example 1 was repeated except that 0.4 g (0.72 mmol) of compound t obtained in Reference Example 18, 0.29 ml (3.61 mmol) of 2-aminobutanol, and 0.23 ml (3.1 mmol) of thionyl chloride were used to obtain 0.11 g (yield: 24%) of titled compound 30 as a brown solid.

$^1$H-NMR (DMSO-d$_6$) δ (ppm); 8.03–7.12(m, 8H), 5.25(s, 2H), 4.47–4.31(m, 2H), 3.98–3.87(m, 1H), 1.81–1.70(m, 2H), 0.98(t, J=7.9 Hz, 3H) MS(m/e); 577 (M$^+$)

IR(KBr, cm$^{-1}$); 1716, 1700, 1683, 1587 Melting point; 217.5–219.5° C. Elementary analysis; For C$_{22}$H$_{19}$N$_5$OIBr 1.7 HCl. Found (%): C, 41.54; H, 3.46; N, 10.63. Calculated (%): C, 41.40; H, 3.27; N, 10.97.

EXAMPLE 31

2-(p-Bromophenyl)-4-(3-iodobenzyl)-1,4,5,7,8,9-hexahydropyrimido[2,1-i]purine-5-one (Compound 31)

Example 1 was repeated except that 0.4 g (0.72 mmol) of compound t obtained in Reference Example 18, 0.29 ml (3.61 mmol) of 2-aminobutanol, and 0.23 ml (3.1 mmol) of thionyl chloride were used to obtain a hydrochloride of titled compound 31. To the thus-obtained hydrochloride were added chloroform and a 1N sodium hydroxide aqueous solution to extract an organic layer. The organic layer was dried over anhydrous magnesium sulfate, and the solvent was distilled off under reduced pressure, followed by recrystallization from ethanol to obtain 0.15 g (yield: 35%) of titled compound 31 as a pale brown solid.

$^1$H-NMR (CDCl$_3$) δ (ppm); 8.08(d, J=8.4 Hz, 2H), 8.00(s, 1H), 7.64–7.59(m, 1H), 7.54(d, J=8.4 Hz, 2H), 7.06(t, J=7.4 Hz, 1H), 5.32(s, 2H), 4.03(t, J=5.9 Hz, 2H), 3.22(t, J=5.4 Hz, 2H), 2.09–2.00(m, 2H) MS(m/e); 561 (M$^+$)

IR(KBr, cm$^{-1}$); 1716, 1683, 1652, 1558 Melting point; 287.5–290.0° C. Elementary analysis; For C$_{21}$H$_{17}$N$_5$OIBr 0.4 C$_2$H$_5$OH, 0.8H$_2$O, Found (%): C, 44.00; H, 3.26; N, 11.50. Calculated (%): C, 44.00; H, 3.55; N, 11.77.

EXAMPLE 32

(R)-2-(p-Bromophenyl)-8-isopropyl-4-propyl-1,4,7,8-tetrahydro-5H-imidazo[2,1-i]purine-5-one (Compound 32)

Example 1 was repeated except that 2.0 g (5.29 mmol) of compound f obtained in Reference Example 6, 2.92 ml (26.45 mmol) of (R)-(−)-2-amino-3-methyl-1-butanol, and 3.11 ml (42.6 mmol) of thionyl chloride were used to obtain a hydrochloride of titled compound 32. To the thus-obtained hydrochloride were added chloroform and a 1N sodium hydroxide aqueous solution to extract an organic layer. The organic layer was dried over anhydrous magnesium sulfate, and the solvent was distilled off under reduced pressure, followed by recrystallization from ethanol to obtain 0.72 g (yield: 33%) of titled compound 32 as a white solid.

$^1$H-NMR (DMSO-d$_6$) δ (ppm); 8.03(d, J=8.4 Hz, 2H), 7.60(d, J=8.4 Hz, 2H), 4.25–3.99(m, 4H), 3.88–3.82(m, 1H), 1.93–1.85(m, 1H), 1.76(q, J=7.4 Hz 2H), 0.97–0.87(m, 9H) MS(m/e); 417, 415 (M$^+$)

IR(KBr, cm$^{-1}$); 1700, 1687, 1546, 1265 Melting point; 156.5–157.5° C. Elementary analysis; For C$_{19}$H$_{22}$N$_5$OBr 0.5 C$_2$H$_5$OH, 0.5H$_2$O. Found (%): C, 53.67; H, 5.86; N, 15.58. Calculated (%): C, 53.58; H, 5.84; N, 15.62.

EXAMPLE 33

(S)-2-(p-Bromophenyl)-8-isopropyl-4-propyl-1,4,7,8-tetrahydro-5H-imidazo[2,1-i]purine-5-one (Compound 33)

Example 1 was repeated except that 2.0 g (5.29 mmol) of compound f obtained in Reference Example 6, 2.73 g (26.45 mmol) of (S)-(+)-2-amino-3-methyl-1-butanol, and 1.51 ml (20.75 mmol) of thionyl chloride were used to obtain a hydrochloride of titled compound 33. To the thus-obtained hydrochloride were added chloroform and a 1N sodium hydroxide aqueous solution to extract an organic layer. The organic layer was dried over anhydrous magnesium sulfate, and the solvent was distilled off under reduced pressure, followed by recrystallization from ethanol to obtain 1.08 g (yield: 49%) of titled compound 33 as a white solid.

$^1$H-NMR (DMSO-d$_6$) δ (ppm); 10.20s(br), 1H), 8.03(d, J=8.4 Hz, 2H), 7.60(d, J=8.4 Hz, 2H), 4.25–3.99(m, 4H), 3.88–3.82(m, 1H), 1.95–1.69(m, 3H), 0.99–0.89(m, 9H) MS(m/e); 417, 415 (M$^+$)

IR(KBr, cm$^{-1}$); 1706, 1664, 1542, 1265 Melting point; 279.3–279.7° C. Elementary analysis; For C$_{19}$H$_{22}$N$_5$OBr 0.7 C$_2$H$_5$OH 0.6H$_2$O. Found (%): C, 53.45; H, 5.91; N, 15.16. Calculated (%): C, 53.34; H, 6.01; N, 15.26.

EXAMPLE 34

(S)-2-(p-Bromophenyl)-8-phenyl-4-propyl-1,4,7,8-tetrahydro-5H-imidazo[2,1-i]purine-5-one (Compound 34)

Example 1 was repeated except that 0.2 g (0.53 mmol) of compound f obtained in Reference Example 6, 290 mg (2.11 mmol) of (S)-(+)-phenylglycinol, and 0.15 ml (21.2 mmol) of thionyl chloride were used to obtain a hydrochloride of titled compound 34. To the thus-obtained hydrochloride were added chloroform and a 1N sodium hydroxide aqueous solution to extract an organic layer. The organic layer was dried over anhydrous magnesium sulfate, and the solvent was distilled off under reduced pressure, followed by recrystallization from ethanol to obtain 0.10 g (yield: 42%) of titled compound 34 as a white solid.

$^1$H-NMR (DMSO-d$_6$) δ (ppm); 8.08–7.81(m, 4H), 7.57–7.41(m, 5H), 5.66–5.59(m, 1H), 4.75(t, J=10.9 Hz, 1H), 4.12–3.98(m, 3H), 1.79(q, J=7.4 Hz, 2H), 0.97(t, J=7.4 Hz, 3H) MS(m/e); 451, 449 (M$^+$)

IR(KBr, cm$^{-1}$); 1697, 1670, 1546, 1263 Melting point; 168.5–170.3° C. Elementary analysis; For C$_{22}$H$_{20}$N$_5$OBr 0.5 C$_2$H$_5$OH, 1.2H$_2$O. Found (%): C, 55.81; H, 4.84; N, 14.03. Calculated (%): C, 55.81; H, 5.17; N, 14.15.

EXAMPLE 35

(R)-2-(p-Bromophenyl)-8-phenyl-4-propyl-1,4,7,8-tetrahydro-5H-imidazo[2,1-i]-purine-5-one (Compound 35)

Example 1 was repeated except that 0.2 g (0.53 mmol) of compound f obtained in Reference Example 6, 290 mg (2.11 mmol) of (R)-(−)-phenylglycinol, and 0.15 ml (21.2 mmol) of thionyl chloride were used to obtain a hydrochloride of titled compound 35. To the thus-obtained hydrochloride were added chloroform and a 1N sodium hydroxide aqueous solution to extract an organic layer. The organic layer was dried over anhydrous magnesium sulfate, and the solvent was distilled off under reduced pressure, followed by recrystallization from ethanol to obtain 0.08 g (yield: 34%) of titled compound 35 as a white solid.

$^1$H-NMR (DMSO-d$_6$) δ (ppm); 8.10–7.81(m, 4H), 7.58–7.39(m, 5H), 5.67–5.60(m, 1H), 4.76(t, J=10.9 Hz, 1H), 4.13–3.98(m, 3H), 1.79(q, J=7.4 Hz, 2H), 0.97(t, J=7.4 Hz, 3H) MS(m/e); 451, 449 (M$^+$)

IR(KBr, cm$^{-1}$); 1697, 1670, 1652, 1540 Melting point; 168.8–170.2° C. Elementary analysis; For C$_{22}$H$_{20}$N$_5$OBr 0.5 C$_2$H$_5$OH, 0.7H$_2$O. Found (%): C, 56.92; H, 4.99; N, 14.34. Calculated (%): C, 56.84; H, 5.06; N, 14.41.

EXAMPLE 36

8-Ethyl-2-(3-iodophenyl)-4-propyl-1,4,7,8-tetrahydro-5H-imidazo[2,1-i]purine-5-one hydrochloride (Compound 36)

Example 1 was repeated except that 0.3 g (0.70 mmol) of compound u obtained in Reference Example 19, 0.28 ml (3.52 mmol) of 2-aminobutanol, and 0.47 ml (6.67 mmol) of thionyl chloride were used to obtain 0.25 g (yield: 74%) of titled compound 36 as a solid.

$^1$H-NMR (DMSO-d$_6$) δ (ppm); 8.44s (br), 1H), 8.12(d (br), J=7.6 Hz, 1H), 95(d, J=7.6 Hz, 2H), 7.41(t, J=7.6 Hz, 1H), 7.41(t, J=7.9Hz, 1H), 4.05–3.72(m, 5H), 1.80–1.71(m, 4H), 1.01–0.91(m, 6H) MS(m/e); 449 (M$^+$)

IR(KBr, cm$^{-1}$); 1741, 1712, 1646, 1558 Melting point; 218.0–220.0° C. Elementary analysis; For C$_{18}$H$_{20}$N$_5$OI 0.7 HCl 0.6H$_2$O. Found (%): C, 44.55; H, 4.50; N, 14.11. Calculated (%): C, 44.52; H, 4.55; N, 14.42.

EXAMPLE 37

2-(2-Furyl)-4-propyl-1,4,7,8-tetrahydro-5H-imidazo-[2,1-i]purine-5-one hydrochloride (Compound 37)

Example 1 was repeated except that 300 mg (1.04 mmol) of compound v obtained in Reference Example 20, 0.44 ml (7.27 mmol) of 2-aminoethanol, and 1 ml (13.71 mmol) of thionyl chloride were used to obtain 159 mg (yield: 54%) of titled compound 37 as a solid. MS(m/e); 285 (M$^+$)

IR(KBr, cm$^{-1}$); 1716, 1677, 1511 Melting point; 235.5–238.0° C.

EXAMPLE 38

8-Ethyl-2-(2-furyl)-4-propyl-1,4,7,8-tetrahydro-5H-imidazo [2,1-i]purine-5-one hydrochloride (Compound 38)

Example 1 was repeated except that 300 mg (1.04 mmol) of compound v obtained in Reference Example 20, 0.69 ml (7.27 mmol) of 2-aminobutanol, and 1 ml (13.71 mmol) of thionyl chloride were used to obtain 40 mg (yield: 12%) of titled compound 38 as a solid. MS(m/e); 313 (M$^+$)

IR(KBr, cm$^{-1}$); 1712, 1677, 1511 Melting point; 205.0–206.5° C.

Reference Example 1

8-(p-Bromophenyl)-3-ethylxanthine (compound a)

5.70 g (28.53 mmol) of p-bromobenzoic acid was suspended in a solvent mixture of 100 ml of dimethylformamide and 100 ml of dichloromethane, and 4.90 g (32.60 mmol) of 1-hydroxybenzotriazole and 7.80 g (40.76 mmol) of 1-ethyl-3-(3-dimethylaminopropyl) carbodiimide hydrochloride were added in turn to the resultant suspension, followed by stirring at room temperature for 5 minutes. Next, to the suspension was added 5.0 g (27.17 mmol) of 5,6-diamino-1-ethyl-2,4-(1H,3H)-pyrimidinedione (Japanese Unexamined Patent Publication No. 80-57517), followed by stirring at room temperature overnight. After dichloromethane was distilled off under reduced pressure, the residue was poured into 600 ml of water. The insoluble substance was filtered off, dried under reduced pressure, and then suspended in a solvent mixture of 100 ml of 4N sodium hydroxide aqueous solution and 100 ml of ethanol, followed by heating under reflux for 2 hours. The reaction solution was cooled to room temperature, and then neutralized with conc. hydrochloric acid. Then the crystals obtained were collected off, and dried under reduced pressure to obtain 6.78 g (yield: 79%) of titled compound a.

$^1$H-NMR (DMSO-d$_6$) δ (ppm); 13.91s(br) 1H), 12.08s (br), 1H), 8.06(d, J=7.9 Hz, 2H), 7.73(d, J=7.9 Hz, 2H), 4.10–3.95(m, 2H), 1.35–1.20(m, 3H) MS(m/e); 336, 334 (M$^+$)

Reference Example 2

8-(p-Bromophenyl)-3-ethyl-6-thioxanthine (compound b)

2.5 g (7.48 mmol) of compound a obtained in Reference Example 1 was heated in 50 ml of pyridine together with 2.66 g (11.9 mmol) of phosphorus pentasulfide and 1.66 ml (11.9 mmol) of triethylamine under reflux for 4 hours. The reaction solution was poured into 200 ml of ice-water, and the precipitated crystals were collected off, and washed well with water and then ether. The thus-obtained crystals were dried under reduced pressure to obtain 2.22 g (yield: 85%) of titled compound b.

$^1$H-NMR (DMSO-d$_6$) δ (ppm); 13.86s(br), 1H), 12.23s (br), 1H), 8.18(d, J=8.6 Hz, 2H), 7.73(d, J=8.6 Hz, 2H), 4.05(q, J=6.9 Hz, 2H), 1.28(t, J=6.9 Hz, 3H)) MS(m/e); 352, 350 (M$^+$)

Reference Example 3

8-(p-Bromophenyl)-3-ethyl-6-methylthio-3-dihydro-2H-purine-2-one (compound c)

10 g (28.57 mmol) of compound b obtained in Reference Example 2 was dissolved in a solvent mixture of 100 ml of ethanol and 100 ml of 2N sodium hydroxide aqueous solution, and 2.67 ml (42.8 mmol) of iodomethane was slowly added to the resultant solution under ice cooling, followed by stirring at room temperature for 1 hour. The solution was neutralized with conc. hydrochloric acid, and the obtained crystals were collected and dried under reduced pressure to obtain 10.8 g (yield: quantitative) of titled compound c.

$^1$H-NMR (DMSO-d$_6$) δ (ppm); 13.69s (br), 1H), 8.11(d, J=8.4 Hz, 2H), 7.77(d, J=8.4 Hz, 2H), 4.14(q, J=6.9 Hz, 2H), 3.31(s, 3H), 1.27(t, J=6.9 Hz, 3H) MS(m/e); 364 (M$^+$)

Reference Example 4

8-(p-Bromophenyl)-3-propylxanthine (compound d)

Reference Example 1 was repeated except that 45 g (240 mmol) of 5,6-diamino-1-propyl-2,4-(1H,3H)-pyrimidinedione U.S. Pat. No. 4,804,664 and U.S. Pat. No. 4,325,956 was used in place of 5,6-diamino-1-ethyl-2,4-(1H,3H)-pyrimidinedione to obtain 63.7 g (yield: 74%) of titled compound d as a white powder.

$^1$H-NMR (DMSO-d$_6$) δ (ppm); 13.86s(br), 1H), 12.23s (br), 1H), 8.18(d, J=8.5 Hz, 2H), 7.73(d, J=8.5 Hz, 2H), 3.95(q, J=7.3 Hz, 3H), 1.73(q, J=7.3 Hz, 2H), 0.91(t, J=7.3 Hz, 3H) MS(m/e); 350, 348 (M$^+$)

Reference Example 5

8-(p-Bromophenyl)-3-propyl-6-thioxanthine (compound e)

Reference Example 2 was repeated except that 50 g (144 mmol) of compound d obtained in Reference Example 4 was used to obtain 44.9 g (yield: 86%) of titled compound e.

¹H-NMR (DMSO-d₆) δ (ppm); 13.84(s, 1H), 12.30(s, 1H), 8.18(d, J=8.9 Hz, 2H), 7.74(d, J=8.9 Hz, 2H), 3.98(t, J=7.3 Hz, 2H), 1.79–1.70(m, 2H), 0.92(t, J=7.3 Hz, 3H) MS(m/e); 366, 364 (M⁺)

Reference Example 6

8-(p-Bromophenyl)-6-methylthio-3-propyl-3-dihydro-2H-purine-2-one (compound f)

Reference Example 3 was repeated except that 20 g (55.0 mmol) of compound e obtained in Reference Example 5 was used to obtain 21.0 g (yield: quantitative) of titled compound f.

¹H-NMR (DMSO-d₆) δ (ppm); 8.11(d, J=8.4 Hz, 2H), 7.77(d, J=8.4 Hz, 2H), 4.05(t, J=7.4 Hz, 2H), 2.63(s, 3H), 1.72(q, J=7.4 Hz, 2H), 0.91(t, J=7.4 Hz, 3H) MS(m/e); 380, 378 (M⁺)

Reference Example 7

8-(o-Bromophenyl)-3-propylxanthine (compound g)

Reference Example 1 was repeated except that 20.0 g (117.6 mmol) of 5,6-diamino-1-propyl-2,4-(1H,3H)-pyrimidineone U.S. Pat. No. 4,804,664 and U.S. Pat. No. 4,325,956 and 22.9 g (114 mmol) of o-bromobenzoic acid were used to obtain 17.8 g (yield: 39%) of titled compound g.

¹H-NMR (DMSO-d₆) δ (ppm); 11.13(s, 1H), 7.79(d, J=7.9 Hz, 1H), 7.65(d, J=7.4 Hz, 1H), 7.65(dd, J=7.4 Hz, 2.0 Hz, 1H), 7.55–7.42(m, 2H), 3.93(t, J=7.4 Hz, 2H), 1.72(q, J=7.4 Hz, 2H), 0.89(t, J=7.4 Hz, 3H) MS(m/e); 350, 348 (M⁺)

Reference Example 8

8-(o-Bromophenyl)-3-propyl-6-thioxanthine (compound h)

Reference Example 2 was repeated except that 10 g (48.5 mmol) of compound g obtained in Reference Example 7 was used to obtain 26.8 g (yield: quantitative) of titled compound h.

¹H-NMR (DMSO-d₆) δ (ppm); 13.78(s, 1H), 12.35(s, 1H), 7.80(d, J=7.4 Hz, 1H), 7.67(dd, J=7.4 Hz, 2.0 Hz, 1H), 7.56–7.45(m, 2H), 3.96(t, J=6.4 Hz, 2H), 1.72(q, J=7.4 Hz, 2H), 0.90(t, J=7.4 Hz, 3H) MS(m/e); 366, 364 (M⁺)

Reference Example 9

8-(o-Bromophenyl)-6-methylthio-3-propyl-3-dihydro-2H-purine-2-one (compound i)

Reference Example 3 was repeated except that 8.19 g (22.5 mmol) of compound h obtained in Reference Example 8 was used to obtain 7.32 g (yield: 86%) of titled compound i.

¹H-NMR (DMSO-d₆) δ (ppm); 13.76(s, 1H), 7.83(d, J=7.9 Hz, 1H), 7.70(d, J=6.9 Hz, 1H), 7.59–7.47(m, 2H), 4.09–3.98(m, 2H), 2.52(s, 3H), 1.73(q, J=7.4 Hz, 2H), 0.90(t, J=7.4 Hz, 3H) MS(m/e); 380, 378 (M⁺)

Reference Example 10

3-Propyl-8-(p-tolyl)xanthine (compound j)

Reference Example 1 was repeated except that 6.0 g (32.6 mmol) of 5,6-diamino-1-propyl-2,4-(1H,3H)-pyrimidinedione U.S. Pat. No. 4,804,664 and U.S. Pat. No. 4,325,956 and 4.66 g (34.2 mmol) of p-methylbenzoic acid were used to obtain 4.41 g (yield: 48%) of titled compound j.

¹H-NMR (DMSO-d₆) δ (ppm); 13.70(s, 1H), 11.09(s, 1H), 7.99(d, J=8.4 Hz, 2H), 7.31(d, J=8.4 Hz, 2H), 3.95(t, J=6.9 Hz, 2H), 2.36(s, 3H), 1.73(q, J=7.4 Hz, 2H), 0.91(t, J=7.4 Hz, 3H) MS(m/e); 284 (M⁺)

Reference Example 11

3-Propyl-8-(p-tolyl)-6-thioxanthine (compound k)

Reference Example 2 was repeated except that 4.0 g (14.1 mmol) of compound j obtained in Reference Example 10 was used to obtain 3.56 g (yield: 84%) of titled compound k.

¹H-NMR (DMSO-d₆) δ (ppm); 13.64(s, 1H), 12.22(s, 1H), 8.14(d, J=7.9 Hz, 2H), 7.34(d, J=8.4 Hz, 2H), 3.98(t, J=7.4 Hz, 2H), 2.37(s, 3H), 1.75(q, J=7.9 Hz, 2H), 0.92(t, J=7.4 Hz, 3H) MS(m/e); 300 (M⁺)

Reference Example 12

6-Methylthio-3-propyl-8-(p-tolyl)-3-dihydro-2H-purine-2-one (compound m)

Reference Example 3 was repeated except that 3.0 g (10.0 mmol) of compound k obtained in Reference Example 11 was used to obtain 3.1 g (yield: 97%) of titled compound m.

¹H-NMR (DMSO-₆) δ (ppm); 8.08(d, J=8.4 Hz, 2H), 7.37(d, J=8.4 Hz, 2H), 4.06(t, J=6.9 Hz, 2H), 2.62(s, 3H), 2.39s 3H), 1.74(q, J=7.4 Hz, 2H), 0.91(t, J=7.44 Hz, 3H) MS(m/e); 314 (M⁺)

The following compounds were synthesized in the same manner as Reference Examples 1 to 3 using corresponding aryl carboxylic acids and pyrimidine derivatives (Japanese Unexamined Patent Publication No. 80-57517)

Reference Example 13

6-Methylthio-3-propyl-8-(m-bromophenyl)-3-dihydro-2H-purine-2-one (compound o)

Yield: 54%

¹H-NMR (DMSO-₆) δ (ppm); 8.38(s, 1H), 8.18(d, J=7.9 Hz, 1H), 7.73(d, J=7.9 Hz, 1H), 7.52(t, J=7.9 Hz, 1H), 4.06(t, J=7.4 Hz, 2H), 2.64(s, 3H), 1.74(q, J=7.4 Hz, 2H), 0.92(t, J=7.4 Hz, 3H) MS(m/e); 380, 378 (M⁺)

Reference Example 14

6-Methylthio-3-propyl-8-phenyl-3-dihydro-2H-purine-2-one (compound p)

Yield: 27%

¹H-NMR (DMSO-d₆) δ (ppm); 8.22–8.17(m, 2H), 7.60–7.49(m, 3H), 4.08(t, J=7.4 Hz, 2H), 2.65(s, 3H), 1.75 (q, J=7.4 Hz, 2H), 0.92(t, J=7.4 Hz, 3H) MS(m/e); 300 (M⁺)

Reference Example 15

6-Methylthio-3-methyl-8-(p-bromophenyl)-3-dihydro-2H-purine-2-one (compound q)

Yield: 56%

¹H-NMR (DMSO-d₆) δ (ppm); 8.11(d, J=8.4 Hz, 2H), 7.78(d, J=8.4 Hz, 2H), 3.54(s, 3H), 2.66(s, 3H) MS(m/e); 350 (M⁺)

Reference Example 16

6-Methylthio-3-n-butyl-8-(p-bromophenyl)-3-dihydro-2H-purine-2-one (compound r)

Yield: 74

$^1$H-NMR (DMSO-d$_6$) δ (ppm); 8.14(d, J=8.9 Hz, 2H), 7.77(d, J=8.9 Hz, 2H), 4.10(t, J=7.4 Hz, 2H), 2.64(s, 3H), 1.71(q, J=7.4 Hz, 2H), 1.32(q, J=7.4 Hz, 2H), 0.93(t, J=7.4 Hz, 3H) MS(m/e); 392 (M$^+$)

Reference Example 17

6-Methylthio-3-phenyl-8-(p-bromophenyl)-3-dihydro-2H-purine-2-one (compound s)

Yield: 68%

$^1$H-NMR (DMSO-d$_6$) δ (ppm); 8.01(d, J=8.4 Hz, 2H), 7.70(d, J=8.4 Hz, 2H), 7.58–7.43(m, 5H), 2.67(s, 3H) MS(m/e); 412(M$^+$)

Reference Example 18

6-Methylthio-3-(3-iodobenzyl)-8-(p-bromophenyl)-3-dihydro-2H-purine-2-one (compound t)

Yield: 81%

$^1$H-NMR (DMSO-d$_6$) (ppm); 8.54(s, 1H), 8.18(d, J=7.6 Hz, 1H), 7.90(d, J=7.6 Hz, 1H), 7.36(t, J=7.9 Hz, 1H), 4.05(t, J=7.3 Hz, 2H), 2.61(s, 3H), 1.73(q, J=7.3 Hz, 2H), 0.91(t, J=7.6 Hz, 3H) MS(m/e); 551 (M$^+$)

Reference Example 19

6-Methylthio-3-propyl-8-(m-iodophenyl)-3-dihydro-2H-purine-2-one (compound u)

Yield: 64%

$^1$H-NMR (DMSO-d$_6$) δ (ppm); 13.71(s(br), 1H), 8.54(s, 1H), 8.18(d, J=7.6 Hz, 1H), 7.89(d, J=7.6 Hz, 1H), 7.36(t, J=7.6 Hz, 1H), 4.05(t, J=7.3 Hz, 2H), 2.61(s, 3H), 1.74(q, J=7.3 Hz, 2H), 0.91(t, J=7.3 Hz, 3H) MS(m/e); 426 (M$^+$)

Reference Example 20

6-Methylthio-3-propyl-8-(2-furyl)-3-dihydro-2H-purine-2-one (compound v)

Yield: 87%

$^1$H-NMR (DMSO-d$_6$) δ (ppm); 13.80s(br), 1H), 7.97(s, 1H), 7.30(s, 1H), 6.75–6.74(m, 1H), 4.01(t, J=7.4 Hz, 2H), 2.60(s, 3H), 1.71(q, J=7.4 Hz, 2H), 0.90(t, J=7.4 Hz, 3H) MS(m/e); 290 (M$^+$)

Formulation Example 1

Tablet:

A tablet comprising the following composition is prepared by a normal method.

| | |
|---|---|
| Compound 1 | 10 mg |
| Lactose | 30 mg |
| Potato starch | 15 mg |
| Polyvinyl alcohol | 1.5 mg |
| Magnesium stearate | 0.5 mg |

Formulation Example 2

Capsule:

A capsule comprising the following composition is prepared by a normal method.

| | |
|---|---|
| Compound 1 | 10 mg |
| Lactose | 100 mg |
| Magnesium stearate | 2.5 mg |

These ingredients are mixed and filled in a gelatin capsule.

Formulation Example 3

Injection:

An injection comprising the following composition is prepared by a normal method.

| | |
|---|---|
| Compound 1 | 2 mg |
| Purified soybean oil | 200 mg |
| Purified yolk lecithin | 24 mg |
| Injection glycerin | 50 mg |
| Injection distilled water | 1.72 ml |

Industrial Applicability

The present invention can provide condensed purine derivatives exhibiting adenosine A$_3$ antagonising activity and having an antiasthmatic action, a bronchodilator action, an antiitching action, etc. Compounds (I) according the present invention are useful for treating or preventing diseases such as asthma, allergic rhinitis, hypersensitivity angiitis, atopic dermatitis, psoriasis, urticaria, etc.

What is claimed is:

1. A condensed purine derivative or a pharmacologically acceptable salt thereof, represented by the following formula (I):

(I)

wherein R$^1$ represents (I) aryl unsubstituted or substituted with 1 to 3 substituents which are the same or different, and are selected from the group consisting of (i) lower alkyl unsubstituted or substituted with 1 to 3 substituents which are the same or different, and are selected from the group consisting of carboxy, sulfo, lower alkyl esters, aralkyl esters or aryl esters thereof, hydroxy, and halogen, (ii) lower alkenyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iii) lower alkynyl unsubstituted or substituted with 1 to 3 substituents which are the same or different, and are selected from the group consisting of carboxy, sulfo, lower alkyl esters or aryl esters thereof, hydroxy, and halogen, (iv) aralkyl unsubstituted or substituted with 1 to 3 substituents which are the same or different, and are selected from the group consisting of lower alkyl, hydroxy, and halogen, (v) aryl unsubstituted or substituted with 1 to 3 substituents which are the same or different, and are selected from the group consisting of lower alkyl, hydroxy, and halogen, (vi) hydroxy, (vii) lower alkoxy unsubstituted or substituted with 1 to 3 substituents which are the same or different, and are selected from the group consisting of carboxy, sulfo, lower alkyl esters, aralkyl esters or aryl esters thereof, hydroxy, and halogen, (viii) aralkyloxy unsubstituted or substituted with 1 to 3 substituents which are the same or different, and are selected from the group consisting of lower alkyl, hydroxy, and halogen, (ix) aryloxy unsubstituted or substituted with 1 to 3 substituents which are the same or different, and are selected from the group consisting of lower alkyl, hydroxy, and halogen, (x) lower alkoxycarbonyl, (xi) lower alkylthio, (xii) lower alkylsulfonyl, (xiii) carboxy, (xiv) carbamoyl, (xv) lower alkanoyl, (xvi) aroyl, (xvii) halogen, (xviii) nitro, (xix) amino, (xx) mono- or di-lower alkylamine, (xxi) cyano, and (xxii) trifluoromethyl, or (II) an aromatic heterocyclic group unsubstituted or substituted with 1 to 3 substituents which are the same or different, and are selected from the group consisting of (i) lower alkyl unsubstituted or substituted with 1 to 3 substituents which are the same or different, and are selected from the group consisting of carboxy, sulfo, lower alkyl esters, aralkyl esters or aryl esters thereof, hydroxy, and halogen, (ii) lower alkenyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iii) lower alkynyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iv) aralkyl unsubstituted or substituted with 1 to 3 substituents which are the same or different, and are selected from the group consisting of lower alkyl, hydroxy, and halogen, (v) aryl unsubstituted or substituted with 1 to 3 substituents which are the same or different, and are selected from the group consisting of lower alkyl, hydroxy, and halogen, (vi) hydroxy, (vii) lower alkoxy unsubstituted or substituted with 1 to 3 substituents which are the same or different, and are selected from the group consisting of carboxy, sulfo, lower alkyl esters, aralkyl esters or aryl esters thereof, hydroxy, and halogen, (viii) aralkyloxy unsubstituted or substituted with 1 to 3 substituents which are the same or different, and are selected from the group consisting of lower alkyl, hydroxy, and halogen, (ix) aryloxy unsubstituted or substituted with 1 to 3 substituents which are the same or different, and are selected from the group consisting of lower alkyl, hydroxy, and halogen, (x) lower alkoxycarbonyl, (xi) lower alkylthio, (xii) lower alkylsulfonyl, (xiii) carboxy, (xiv) carbamoyl, (xv) lower alkanoyl, (xvi) aroyl, (xvii) halogen, (xviii) nitro, (xix) amino, (xx) mono- or di-lower alkylamine, (xxi) cyano, and (xxii) trifluoromethyl;

$R^2$ represents
(I) hydrogen,
(II) lower alkyl,
(III) alicyclic alkyl,
(IV) aralkyl unsubstituted or substituted with 1 to 3 substituents which are the same or different, and are selected from the group consisting of (i) lower alkyl unsubstituted or substituted with 1 to 3 substituents which are the same or different, and are selected from the group consisting of carboxy, sulfo, lower alkyl esters, aralkyl esters or aryl esters thereof, hydroxy, and halogen, (ii) lower alkenyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iii) lower alkynyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iv) aralkyl unsubstituted or substituted with 1 to 3 substituents which are the same or different, and are selected from the group consisting of lower alkyl, hydroxy, and halogen, (v) aryl unsubstituted or substituted with 1 to 3 substituents which are the same or different, and are selected from the group consisting of lower alkyl, hydroxy, and halogen, (vi) hydroxy, (vii) lower alkoxy unsubstituted or substituted with 1 to 3 substituents which are the same or different, and are selected from the group consisting of carboxy, sulfo, lower alkyl esters, aralkyl esters or aryl esters thereof, hydroxy, and halogen, (viii) aralkyloxy unsubstituted or substituted with 1 to 3 substituents which are the same or different, and are selected from the group consisting of lower alkyl, hydroxy, and halogen, (ix) aryloxy unsubstituted or substituted with 1 to 3 substituents which are the same or different, and are selected from the group consisting of lower alkyl, hydroxy, and halogen, (x) lower alkoxycarbonyl, (xi) lower alkylthio, (xii) lower alkylsulfonyl, (xiii) carboxy, (xiv) carbamoyl, (xv) lower alkanoyl, (xvi) aroyl, (xvii) halogen, (xviii) nitro, (xix) amino, (xx) mono- or di-lower alkylamine, (xxi) cyano, and (xxii) trifluoromethyl, (V) aryl unsubstituted or substituted with 1 to 3 substituents which are the same or different, and are selected from the group consisting of (i) lower alkyl unsubstituted or substituted with 1 to 3 substituents which are the same or different, and are selected from the group consisting of carboxy, sulfo, lower alkyl esters, aralkyl esters or aryl esters thereof, hydroxy, and halogen, (ii) lower alkenyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iii) lower alkynyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iv) aralkyl unsubstituted or substituted with 1 to 3 substituents which are the same or different, and are selected from the group consisting of lower alkyl, hydroxy, and halogen, (v) aryl unsubstituted or substituted with 1 to 3 substituents which are the same or different, and are selected from the group consisting of lower alkyl, hydroxy, and halogen, (vi) hydroxy, (vii) lower alkoxy unsubstituted or substituted with 1 to 3 substituents which are the same or different, and are selected from the group consisting of carboxy, sulfo, lower alkyl esters, aralkyl esters or aryl esters thereof, hydroxy, and halogen, (viii) aralkyloxy unsubstituted or substituted with 1 to 3 substituents which are the same or different, and are selected from the group consisting of lower alkyl, hydroxy, and halogen, (ix) aryloxy unsubstituted or substituted with 1 to 3 substituents which are the same or different, and are selected from the group consisting of lower alkyl, hydroxy, and halogen, (x) lower alkoxycarbonyl, (xi) lower alkylthio, (xii) lower alkylsulfonyl, (xiii) carboxy, (xiv) carbamoyl, (xv) lower alkanoyl, (xvi) aroyl, (xvii) halogen, (xviii) nitro, (xix) amino, (xx) mono- or di-lower alkylamine, (xxi) cyano, and (xxii) trifluoromethyl, or (VI) an aromatic heterocyclic group unsubstituted or substituted with 1 to 3 substituents which are the same or different, and are selected from the group consisting of (i) lower alkyl unsubstituted or substituted with 1 to 3 substituents which are the same or different, and are selected from the group consisting of carboxy, sulfo, lower alkyl esters, aralkyl esters or aryl esters thereof, hydroxy, and halogen, (ii) lower alkenyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iii) lower alkynyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iv) aralkyl unsubstituted or substituted with 1 to 3 substituents which are the same or different, and are selected from the group consisting of lower alkyl, hydroxy, and halogen, (v) aryl unsubstituted or substituted with 1 to 3 substituents which are the same or different, and are selected from the group consisting of lower alkyl, hydroxy, and halogen, (vi) hydroxy, (vii) lower alkoxy unsubstituted or substituted with 1 to 3 substituents which are the same or different, and are selected from the group consisting of carboxy, sulfo, lower alkyl esters, aralkyl esters or aryl esters thereof, hydroxy, and halogen, (viii) aralkyloxy unsubstituted or substituted with 1 to 3 substituents which are the same or different, and are selected from the group consisting of lower alkyl, hydroxy, and halogen, (ix) aryloxy unsubstituted or substituted with 1 to 3 substituents which are the same or different, and are selected from the group consisting of lower alkyl, hydroxy, and halogen, (x) lower alkoxycarbonyl, (xi) lower alkylthio, (xii) lower alkylsulfonyl, (xiii) carboxy, (xiv) carbamoyl, (xv) lower alkanoyl, (xvi) aroyl, (xvii) halogen, (xviii) nitro, (xix) amino, (xx) mono- or di-lower alkylamine, (xxi) cyano, and (xxii) trifluoromethyl;

$R^3$ represents
(I) hydrogen,
(II) lower alkyl, or
(III) aralkyl unsubstituted or substituted with 1 to 3 substituents which are the same or different, and are selected from the group consisting of (i) lower alkyl unsubstituted or substituted with 1 to 3 substituents which are the same or different, and are selected from the group consisting of carboxy, sulfo, lower alkyl esters, aralkyl esters or aryl esters thereof, hydroxy, and halogen, (ii) lower alkenyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iii) lower alkynyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iv) aralkyl unsubstituted or substituted with 1 to 3 substituents which are the same or different, and are selected from the group consisting of lower alkyl, hydroxy, and halogen, (v) aryl unsubstituted or substituted with 1 to 3 substituents which are the same or different, and are selected from the group consisting of lower alkyl, hydroxy, and halogen, (vi) hydroxy, (vii) lower alkoxy unsubstituted or substituted with 1 to 3 substituents which are the same or different, and are selected from the group consisting of carboxy, sulfo, lower alkyl esters, aralkyl esters or aryl esters thereof, hydroxy, and halogen, (viii) aralkyloxy unsubstituted or substituted with 1 to 3 substituents which are the same or different, and are selected from the group consisting of lower alkyl, hydroxy, and halogen, (ix) aryloxy unsubstituted or substituted with 1 to 3 substituents which are the same or different, and are selected from the group consisting of lower alkyl, hydroxy, and halogen, (x) lower alkoxycarbonyl, (xi) lower alkylthio, (xii) lower alkylsulfonyl, (xiii) carboxy, (xiv) carbamoyl, (xv) lower alkanoyl, (xvi) aroyl, (xvii) halogen, (xviii) nitro, (xix) amino, (xx) mono- or di-lower alkylamine, (xxi) cyano, and (xxii) trifluoromethyl;

$X^1$ and $X^2$ are the same or different and each represents
(I) hydrogen,
(II) lower alkyl,
(III) aralkyl unsubstituted or substituted with 1 to 3 substituents which are the same or different, and are selected from the group consisting of (i) lower alkyl unsubstituted or substituted with 1 to 3 substituents which are the same or different, and are selected from the group consisting of carboxy, sulfo, lower alkyl esters, aralkyl esters or aryl esters thereof, hydroxy, and halogen, (ii) lower alkenyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iii) lower alkynyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iv) aralkyl unsubstituted or substituted with 1 to 3 substituents which are the same or different, and are selected from the group consisting of lower alkyl, hydroxy, and halogen, (v) aryl unsubstituted or substituted with 1 to 3 substituents which are the same or different, and are selected from the group consisting of lower alkyl, hydroxy, and halogen, (vi) hydroxy, (vii) lower alkoxy unsubstituted or substituted with 1 to 3 substituents which are the same or different, and are selected from the group consisting of carboxy, sulfo, lower alkyl esters, aralkyl esters or aryl esters thereof, hydroxy, and halogen, (viii) aralkyloxy unsubstituted or substituted with 1 to 3 substituents which are the same or different, and are selected from the group consisting of lower alkyl, hydroxy, and halogen, (ix) aryloxy unsubstituted or substituted with 1 to 3 substituents which are the same or different, and are selected from the group consisting of lower alkyl, hydroxy, and halogen, (x) lower alkoxycarbonyl, (xi) lower alkylthio, (xii) lower alkylsulfonyl, (xiii) carboxy, (xiv) carbamoyl, (xv) lower alkanoyl, (xvi) aroyl, (xvii) halogen, (xviii) nitro, (xix) amino, (xx) mono- or di-lower alkylamine, (xxi) cyano, and (xxii) trifluoromethyl, or (IV) aryl unsubstituted or substituted with 1 to 3 substituents which are the same or different, and are selected from the group consisting of (i) lower alkyl unsubstituted or substituted with 1 to 3 substituents which are the same or different, and are selected from the group consisting of carboxy, sulfo, lower alkyl esters, aralkyl esters or aryl esters thereof, hydroxy, and halogen, (ii) lower alkenyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iii) lower alkynyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iv) aralkyl unsubstituted or substituted with 1 to 3 substituents which are the same or different, and are selected from the group consisting of lower alkyl, hydroxy, and halogen, (v) aryl unsubstituted or substituted with 1 to 3 substituents which are the same or different, and are selected from the group consisting of lower alkyl, hydroxy, and halogen, (vi) hydroxy, (vii) lower alkoxy unsubstituted or substituted with 1 to 3 substituents which are the same or different, and are selected from the group consisting of carboxy, sulfo, lower alkyl esters, aralkyl esters or aryl esters thereof, hydroxy, and halogen, (viii) aralkyloxy unsubstituted or substituted with 1 to 3 substituents which are the same or different, and are selected from the group consisting of lower alkyl, hydroxy, and halogen, (ix) aryloxy unsubstituted or substituted with 1 to 3 substituents which are the same or different, and are selected from the group consisting of lower alkyl, hydroxy, and halogen, (x) lower alkoxycarbonyl, (xi) lower alkylthio, (xii) lower alkylsulfonyl, (xiii) carboxy, (xiv) carbamoyl, (xv) lower alkanoyl, (xvi) aroyl, (xvii) halogen, (xviii) nitro, (xix) amino, (xx) mono- or di-lower alkylamine, (xxi) cyano, and (xxii) trifluoromethyl; and n represents an integer of 0 to 3.

2. The condensed purine derivative or pharmacologically acceptable salt thereof according to claim 1 wherein $R^3$ is hydrogen.

3. The condensed purine derivative or pharmacologically acceptable salt thereof according to claim 2, wherein $R^1$ is phenyl unsubstituted or substituted with 1 to 3 substituents which are the same or different, and are selected from the group consisting of (i) lower alkyl unsubstituted or substituted with 1 to 3 substituents which are the same or different, and are selected from the group consisting of carboxy, sulfo, lower alkyl esters, aralkyl esters or aryl esters thereof, hydroxy, and halogen, (ii) lower alkenyl unsubstituted or substituted with 1 to 3 substituents which are the same or different, and are selected from the group consisting of a carboxy, sulfo, lower alkyl esters, aralkyl esters or aryl esters thereof, hydroxy, and halogen, (iii) lower alkynyl unsubstituted or substituted with 1 to 3 substituents which are the same or different, and are selected from the group consisting of carboxy, sulfo, lower alkyl esters, aralkyl esters or aryl esters thereof, hydroxy, and halogen, (iv) aralkyl unsubstituted or substituted with 1 to 3 substituents which are the same or different, and are selected from the group consisting of lower alkyl, hydroxy, and halogen, (v) aryl unsubstituted or substituted with 1 to 3 substituents which are the same or different, and are selected from the group consisting of lower alkyl, hydroxy, and halogen, (vi) hydroxy, (vii) lower alkoxy unsubstituted or substituted with 1 to 3 substituents which are the same or different, and are selected from the group consisting of carboxy, sulfo, lower alkyl esters, aralkyl esters or aryl esters thereof, hydroxy, and halogen, (viii) aralkyloxy unsubstituted or substituted with 1 to 3 substituents which are the same or different, and are selected from the group consisting of lower alkyl, hydroxy, and halogen, (ix) aryloxy unsubstituted or substituted with 1 to 3 substituents which are the same or different, and are selected from the group consisting of lower alkyl, hydroxy, and halogen, (x) lower alkoxycarbonyl, (xi) lower alkylthio, (xii) lower alkylsulfonyl, (xiii) carboxy, (xiv) carbamoyl, (xv) lower alkanoyl, (xvi) aroyl, (xvii) halogen, (xviii) nitro, (xix) amino, (xx) mono- or di-lower alkylamine, (xxi) cyano, and (xxii) trifluoromethyl.

4. The condensed purine derivative or pharmacologically acceptable salt thereof according to claim 3, wherein the substituted phenyl has 1 to 3 substituents which are the same or different, and are selected from halogen, lower alkyl, lower alkoxy, and lower alkenyl substituted with 1 to 3 substituents which are the same or different, and are selected from the group consisting of carboxy, sulfo, lower alkyl esters, aralkyl esters or aryl esters thereof, hydroxy, and halogen.

5. The condensed purine derivative or pharmacologically acceptable salt thereof according to claim 3, wherein the substituent of substituted lower alkenyl is lower alkoxycarbonyl.

6. The condensed purine derivative or pharmacologically acceptable salt thereof according to claim 3, wherein the substituted phenyl has 1 to 3 substituents which are the same or different and are halogen.

7. A pharmaceutical composition comprising a condensed purine derivative or pharmacologically acceptable salt thereof according to claim 1 and a pharmacologically acceptable carrier.

* * * * *